US012746149B2

(12) United States Patent
Yantis et al.

(10) Patent No.: US 12,746,149 B2
(45) Date of Patent: Sep. 29, 2026

(54) PESSARY INSERTION APPARATUS

(71) Applicant: Lilium Solutions LLC, Scottsdale, AZ (US)

(72) Inventors: Leanne Yantis, Scottsdale, AZ (US); Ryan Michael Welsh Snow, Boulder, CO (US); Sean William Connelly, Boulder, CO (US); Mikaela Marie Leeyi Juzswik, Boulder, CO (US); Maxiliaan Eduard Gulden, Boulder, CO (US); Zachary Speer, Boulder, CO (US)

(73) Assignee: Lilium Solutions LLC, Scottsdale, AZ (US)

( * ) Notice: Subject to any disclaimer, the term of this patent is extended or adjusted under 35 U.S.C. 154(b) by 0 days.

(21) Appl. No.: 19/394,675

(22) Filed: Nov. 19, 2025

(65) Prior Publication Data

US 2026/0137550 A1 May 21, 2026

Related U.S. Application Data

(60) Provisional application No. 63/723,016, filed on Nov. 20, 2024.

(51) Int. Cl.
*A61F 6/12* (2006.01)

(52) U.S. Cl.
CPC .................................... *A61F 6/12* (2013.01)

(58) Field of Classification Search
CPC ...... A61F 6/12; A61F 6/08; A61F 6/06; A61F 6/00; A61F 6/14; A61F 6/146; A61F 6/18; A61F 6/20; A61B 17/12022
See application file for complete search history.

(56) References Cited

U.S. PATENT DOCUMENTS

| | | | | |
|---|---|---|---|---|
| 726,532 | A * | 4/1903 | Hering | A61F 6/08 128/835 |
| 2,008,380 | A * | 7/1935 | Backmann | A61F 6/12 604/60 |
| 2,830,582 | A | 4/1958 | Ljung | |
| 5,934,279 | A | 8/1999 | Lammers | |
| 12,508,170 | B2 * | 12/2025 | Agbo | A61F 5/4553 |
| 2022/0296411 | A1 * | 9/2022 | Maier | A61F 2/005 |

FOREIGN PATENT DOCUMENTS

| | | | | |
|---|---|---|---|---|
| EP | 0044102 | A1 * | 1/1982 | A61F 6/12 |
| EP | 0247837 | A2 | 12/1987 | |
| WO | WO-99/38468 | A1 | 8/1999 | |

* cited by examiner

*Primary Examiner* — Tarla R Patel
(74) *Attorney, Agent, or Firm* — Foley Hoag LLP; Matthew D. Jonsen; Nicole A. Bustos-Pomerantz

(57) ABSTRACT

A pessary insertion apparatus is provided. The apparatus comprises a support member, a handle coupled to a first end of the support member, a rod disposed within the support member, and a pessary-engaging structure disposed at a second end of the support member. The apparatus, may also include a body having a first end and a second end and the support member may be disposed, at least partially, within the body. The pessary-engaging structure is operatively coupled to the first rod end and an actuator is operatively coupled with the second rod end and configured to translate the rod relative to the support member. Translation of the rod causes rotation of the pessary-engaging structure.

18 Claims, 18 Drawing Sheets

PESSARY INSERTION APPARATUS

CROSS-REFERENCE TO RELATED APPLICATIONS

This application claims the benefit of priority to U.S. Provisional App. No. 63/723,016, filed on Nov. 20, 2024, the entire contents of which are hereby incorporated by reference.

BACKGROUND OF THE DISCLOSED SUBJECT MATTER

Field of the Disclosed Subject Matter

The disclosed subject matter relates to apparatuses and methods for pessary insertion. More specifically, the disclosed subject matter relates to pessary insertion apparatuses adapted to aid in the insertion and proper placement of a pessary device.

Many women suffer from pelvic organ prolapse. One of the first options for treatment is a pessary device, to support the organs, preventing or lessening organ shifting. To do this, the pessary must be inserted into the vaginal canal. Typically, the pessary is constructed of a resilient, though rigid material (for example silicone) that permits the pessary to be compacted (in the case of a ring pessary, folded) for the insertion. Generally, the pessary is inserted using the fingers and hands of the user or the doctor.

Insertion of a ring pessary is initiated by first folding the pessary, roughly in half, to create a crescent shape. The crescent is grasped at one end of the curve, such that the two folded ends point downwards, and posteriorly. The pessary is then inserted through the vaginal canal toward the fornix and allowed to unfold. Once inserted, the pessary often must be rotated to ensure that it is properly positioned. Insertion of the pessary is typically a painful process and can be difficult for users with dexterity and/or flexibility limitations. Pessaries must be removed periodically for cleaning, and during certain activities, such as intercourse, x-rays, ultrasounds, or MRI. Therefore, insertion of the pessary is a periodic activity that the user must perform and/or endure repeatedly.

To enhance insertion into the vaginal cavity and comfort during insertion, the pessary is typically covered with a lubricant, which makes the pessary relatively slippery and even more difficult to handle, especially where the pessary must be held in a folded position. These conditions make insertion of the pessary difficult for a doctor and user alike.

Accordingly, there is an urgent need for a device to help a patient and others insert a pessary that makes the insertion of the pessary easier, improves the handling and positioning of the pessary device, provides as much comfort to the patient as possible, and allows more persons to install/re-install the devices on their own, without having to see a healthcare provider.

SUMMARY OF THE DISCLOSED SUBJECT MATTER

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes a pessary insertion apparatus comprising: a body having a first end and a second end; a support member disposed at least partially within the body and having a first end and a second end; a handle coupled to the first end of the support member; a pessary-engaging structure disposed at the second end of the support member; and an actuator operatively coupled to the pessary-engaging structure and configured to translate a force applied to the actuator into rotation of the pessary-engaging structure.

In some embodiments, the pessary-engaging structure comprises a plurality of arms and a middle member, each one of the plurality of arms coupled to the middle member. In some embodiments, at least one of the plurality of arms is joined to the middle member by a living hinge. In some embodiments, the plurality of arms comprises a first arm and a second arm, each extending from the middle member. In some embodiments, the first arm comprises a first and a second curved portion arranged to define a receiving region for retaining a pessary device. In some embodiments, the second arm comprises a planar surface. In some embodiments, the body comprises an opening at the first end of the body and a cap at the second end of the body, the cap having a plurality of compliant flaps configured to flex to allow passage of the pessary-engaging structure. In some embodiments, the body defines a first opening at the first end of the body and a second opening at the second end of the body. In some embodiments, the longitudinal axis of the support member extends longitudinally within the body. In some embodiments, the support arm is configured to translate relative to the body. In some embodiments, the body comprises a guide channel configured to guide translation of the body. In some embodiments, the actuator is disposed on the support member between the pessary-engaging structure and the handle. In some embodiments, the handle is disposed between the pessary-engaging structure and the actuator and the rod extends through the handle. In some embodiments, the pessary insertion apparatus further comprises a rod having a first end and a second end, the first end operatively coupled to the actuator and the second end operatively coupled to the pessary-engaging structure.

The disclosed subject matter also includes a method of operating a pessary insertion device, comprising: providing the pessary insertion apparatus, the pessary insertion apparatus comprising: a body having a first end and a second end, a support member disposed at least partially within the body and configured to translate relative to the body, a handle coupled to the first end of the support member, a pessary-engaging structure disposed at the second end of the support member, wherein the first end of the body is positioned toward the handle and the second end is positioned away from the handle; folding the pessary device; engaging the folded pessary device with the pessary-engaging structure; and positioning the pessary-engaging structure relative to the body of the pessary insertion apparatus to maintain the pessary device in a folded configuration.

In some embodiments, engaging the folded pessary device with the pessary-engaging structure occurs when the pessary-engaging structure is positioned between the first end of the body and the handle. In some embodiments, positioning the pessary-engaging structure relative to the body comprises translating the support member relative to the body such that the pessary-engaging structure moves towards the second end of the body. In some embodiments, engaging the folded pessary device with the pessary-engaging structure occurs when the pessary-engaging structure is positioned beyond the second end of the body. In some embodiments, positioning the pessary-engaging structure relative to the body comprises translating the support member relative to the body such that the pessary-engaging structure moves towards the first end of the body. In some embodiments, the pessary-engaging structure is positioned between the first and second end of the body after positioning. In some embodiments, the method further comprises deploying the pessary device by translating the support member relative to the body such that the pessary-engaging structure becomes exposed through the second end of the body and the pessary device transitions from the folded configuration toward an unfolded configuration.

Also disclosed is a method of deploying a pessary device within a vaginal canal of a subject, comprising folding the pessary device, engaging the folded pessary device with a pessary-engaging structure of a pessary insertion apparatus, maintaining the pessary device in a folded configuration, inserting the pessary-engaging structure into the vaginal canal of the subject until the pessary device is positioned at or near the fornix of the subject, rotating the pessary device relative the pessary insertion apparatus while maintaining engagement between the pessary device and the pessary insertion apparatus before, during, and after rotation, disengaging the pessary device from the pessary insertion apparatus, and withdrawing the insertion apparatus through the vaginal canal.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

DETAILED DESCRIPTION

Figure 1A:
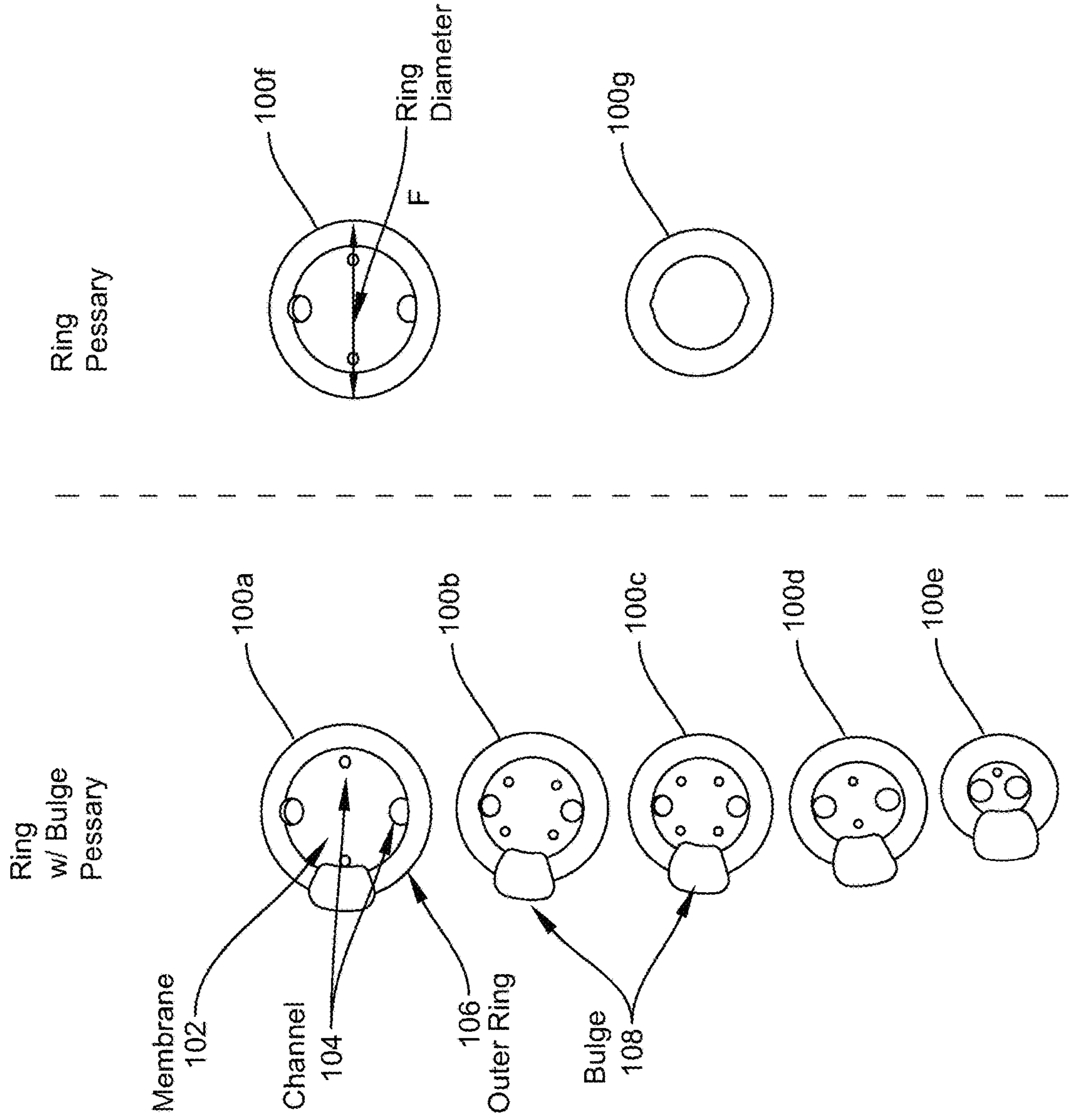
FIG. 1A depicts a view of pessary devices of various embodiments, in accordance with the disclosed subject matter.

The various concepts introduced above and discussed in greater detail below may be implemented in a number of ways, as the described concepts are not limited to any particular manner of embodiment.

Reference will now be made in detail to the exemplary embodiments of the present disclosure, examples of which are illustrated in the accompanying drawings. Wherever possible, the same reference numbers will be used throughout the drawings to refer to the same or like parts.

References herein to positions of elements (e.g., “top”, “bottom”) are merely used to describe the orientation of various elements in the FIGURES. It should be noted that the orientation of various elements may differ according to other embodiments, and that such variations are intended to be encompassed by the present disclosure.

The term "about" means a range of values inclusive of the specified value that a person of ordinary skill in the art would reasonably consider to be comparable to the specified value. In some embodiments, "about" means within a standard deviation using measurements generally accepted by a person of ordinary skill in the art. In some embodiments, "about" means ranging up to ±10% of the specified value. In some embodiments, "about" means ranging up to ±5% of the specified value. In some embodiments, "about" means the specified value.

As used herein, "proximal" refers to the end or direction closer to the handle of the apparatus, and "distal" refers to the opposite end of the apparatus or direction closer to the patient. Unless otherwise indicated, the apparatus is oriented such that the handle is at the proximal end and the pessary-engaging structure is at the distal end.

As used herein, "operatively coupled" refers to a functional coupling between two components such that motion, force, or displacement applied to one component results in a corresponding mechanical action of the other component. The coupling may be direct (e.g., a shared structural interface) or indirect (e.g., via one or more intermediate components), and may be achieved by press-fit engagement, keyed engagement, pivot attachment, sliding engagement, snap-fit, threaded connection, pinned joint, or any other mechanical connection permitting transmission of motion while optionally allowing relative rotation, translation, or flexure as described herein. For example, the actuator of the apparatus can be operatively coupled to the rod such that movement of the actuator causes translation of the rod, and the rod can be operatively coupled to the pessary-engaging structure such that translation of the rod applies a rotational moment to the structure.

As used herein, "folded configuration" refers to the state in which the pessary device is flexed or bent to reduce its width. "Collapsed configuration" refers to the state in which the pessary-engaging structure has its arms pivoted inward to reduce the span of the structure. "Loaded configuration" refers to the state in which the pessary insertion apparatus is holding a folded pessary device with the pessary-engaging structure in the collapsed configuration within the apparatus body. "Deployed configuration" refers to the state in which the pessary-engaging structure is positioned outside of the body of the apparatus and the pessary device is permitted to relax towards its unfolded (expanded) shape.

The present disclosure is directed to pessary insertion apparatuses configured to facilitate preparation, handling, deployment, and insertion of pessary devices. Pessary devices are used to provide support to pelvic organs that have prolapsed and/or require stabilization, including bladder, uterus, rectum, small bowel, or urethra. Conventional insertion techniques often require the patient or medical professional to lubricate, fold, insert, and manually position the pessary device within the vaginal canal. In addition, inserted pessary devices typically must be rotated after positioning in the vaginal canal. Such manual techniques can be difficult, uncomfortable, and/or inconsistent across users. The pessary insertion apparatuses disclosed herein are configured to engage a pessary device in a folded or reduced-width configuration, retain the folded pessary device during insertion and placement, and enable controlled deployment and/or rotation of the pessary device, thereby improving ease of insertion and reducing the dependence on manual manipulation and/or reliance on a second person.

Pessary Devices

Figure 1B:
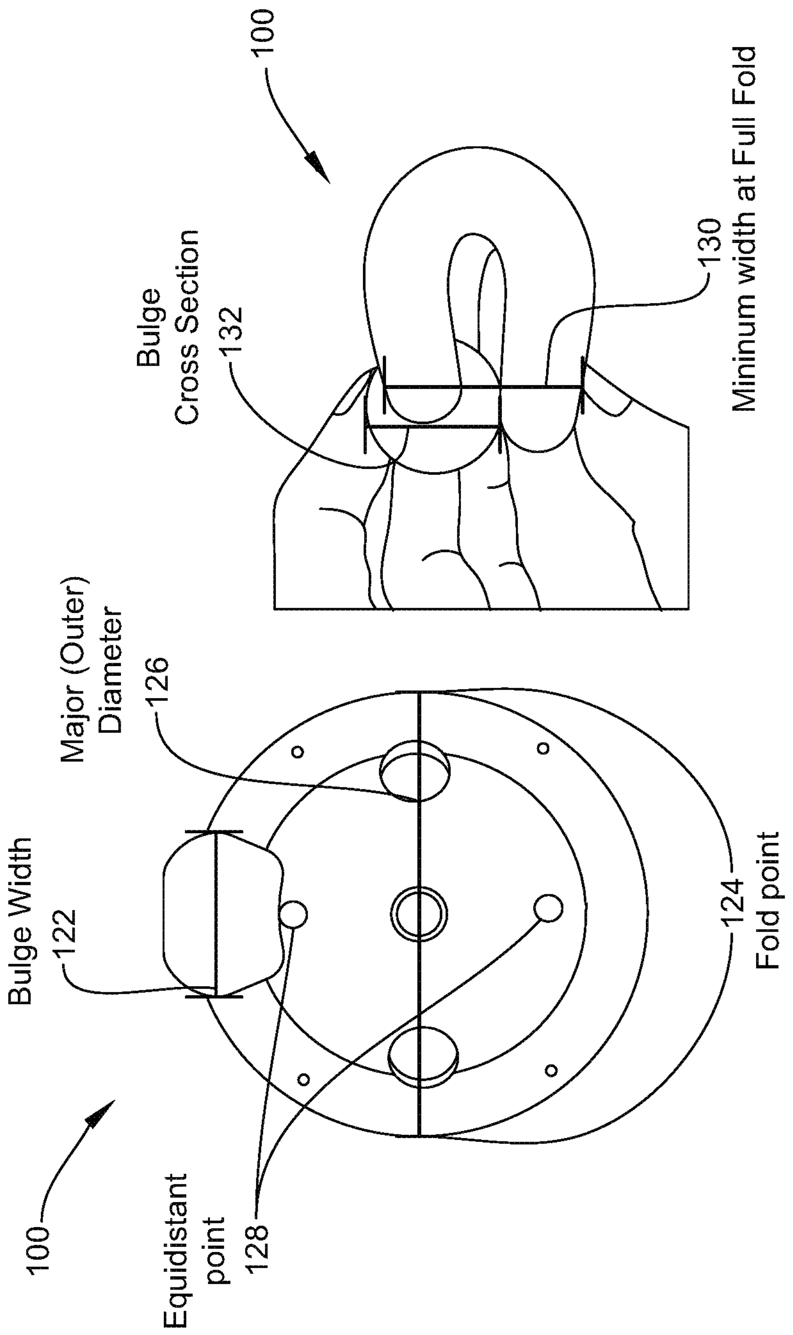
FIG. 1B depicts a top view of a pessary device in an unfolded configuration and a side view of a pessary device in a folded configuration, in accordance with the disclosed subject matter.
Figure 1C:
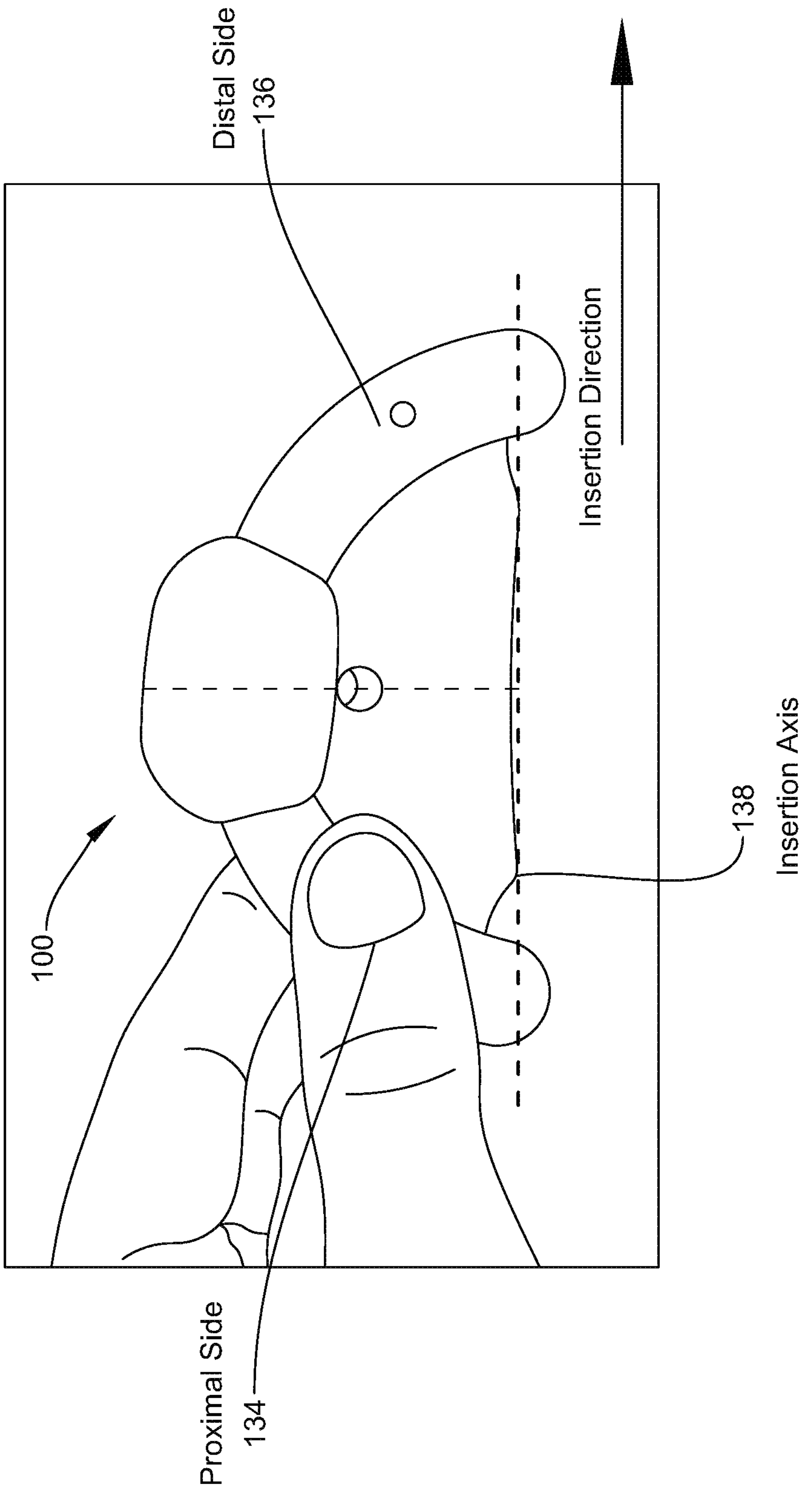
FIG. 1C depicts a view of a pessary device in a folded configuration, in accordance with the disclosed subject matter.

Referring now to FIGS. 1A-1C, various embodiments of pessary devices are illustrated. As shown in FIG. 1A, a pessary device can include an outer ring 102 and, in some embodiments, a membrane 104 extending across at least a portion of the outer ring 102. The membrane 104 can include one or more openings 106 which can allow fluid to pass from one side of the pessary device to the other side. The pessary device can be manufactured from a biocompatible and flexible material, for example, silicon, PVC (vinyl), latex, or a combination thereof.

The membrane 104 can be fixedly attached (e.g., integrally formed) to an inner surface of the outer ring 102, such that the outer ring 102 extends above and below the membrane to define an average thickness of the pessary device. As shown in FIG. 1A, ring diameter can vary across embodiments 100A-100E of pessary devices. Ring pessaries and ring pessaries with a bulge are commonly manufactured in standardized sizes (e.g., sizes 0 through 13), corresponding to outer diameters of about 44 mm to about 127 mm. In some embodiments, the ring diameter is about 50 to about 90 mm. For example, in some embodiments, the ring diameter is about 57 to about 89 mm.

In some embodiments, the outer ring 102 includes a bulge 108. In some embodiments, the bulge 108 is trapezoidal, cylindrical, or spherocylindrical in shape. The bulge 108 can be positioned at various angular locations around the circumference of the outer ring 102 and can project above, below, and/or radially outward of the ring 102. The bulge 108 can provide increased localized thickness or rigidity, and in some embodiments, can define the maximum thickness or outer diameter of the pessary device.

Embodiment 100F depicts a ring pessary without a bulge 108 and including a membrane 104 and one or more openings 106. Embodiment 100G depicts a ring-only pessary formed solely by the outer ring 102, without a membrane or a bulge.

Referring now to FIG. 1B, a top view of a pessary device 100 in an unfolded configuration (left panel) and a side view of the pessary device 100 in a folded configuration (right panel) are shown. In the unfolded configuration, the outer ring 102 extends generally in a plane, and the membrane 104, where present, spans the interior region of the outer ring 102.

The pessary device 100 can be folded to a reduced-width configuration for loading on the apparatus or manual insertion. Folding can be achieved by bending the outer ring 102 at two fold points 124 positioned on opposite sides of the ring, such that points 128 on the membrane 104 (e,g., at or near openings 106, wherein in the unfolded state these points are far from each other, being positioned radially from a fold line intersecting the fold points 124) are brought into proximity, and opposite edges of the ring are brough into contact. During this motion the outer ring 102 assumes a U-shaped or crescent profile and the membrane 104, where present, flexes with the ring without separation. Typically, as shown in FIG. 1B, the bulge is made to contact a point on the opposite side of the ring. In other embodiments, the pessary device may be loaded on the disclosed apparatus in an unfolded state.

In embodiments including a bulge 108, the bulge defines a width 122 and a cross-sectional height, thickness, or curvature 132. The unfolded configuration can define a major (outer) diameter 126; while in the folded configuration the ring can define a minimum folded width 130 corresponding to the reduced-width dimension. These dimensional references are illustrative and can vary with device geometry and material properties.

Referring now to FIG. 1C, a pessary device 100 in the folded configuration is shown held for manual insertion. A proximal side 134 and distal side 136 are illustrated, and an insertion axis 1388 extends from the proximal side 134 toward the distal side 136 (e.g., along a fold line of the device). An insertion direction is also shown with the distal side 136 positioned closest to the vaginal canal. The folded orientation shown in FIG. 1C is illustrative of a conventional configuration for insertion and can similarly be used when the pessary device 100 is engaged with a pessary-engaging structure of a pessary insertion apparatus rather than held by hand.

Pessaries can be inserted manually by folding the device and positioning it within the vaginal canal. Manual insertion can require significant dexterity and strength, and can be difficult for some users, including individuals with limited hand strength, reduced range of motion, or discomfort performing internal placement. Folding and holding the pessary device in a reduce-width configuration while simultaneously guiding it into position can be challenging, and improper handling can lead to the pessary device unfolding prematurely during insertion. These difficulties are often compounded by lubricating the pessary to aid insertion.

Manual insertion can also be limited by the length and reach of the user's fingers, which can restrict achievable insertion depth and in-situ rotation, potentially preventing seating the device as close as desired to the vaginal fornix. This can result in suboptimal seating and the need for repeated attempts to achieve a proper placement.

Accordingly, the present disclosure addresses these issues by providing pessary insertion apparatuses, which help with placement and deployment, minimize or prevent premature unfolding, and more securely grasp even lubricated pessaries, among other advantages.

Pessary Insertion Apparatus

The disclosed pessary insertion apparatus may have various forms. In most embodiments, the pessary insertion apparatus may generally define an extended or rod-like shape configured to engage and hold a pessary device at one end while providing a patient or user engagement structure at the opposite end. In some embodiments, the rod shape may include a user end (proximal end), a body, and a pessary engagement end (distal end). The user and engagement ends are functionally connected such that a force applied at the one end, for example the user end, is translated to the other end, for example the pessary engagement end.

Figure 2:
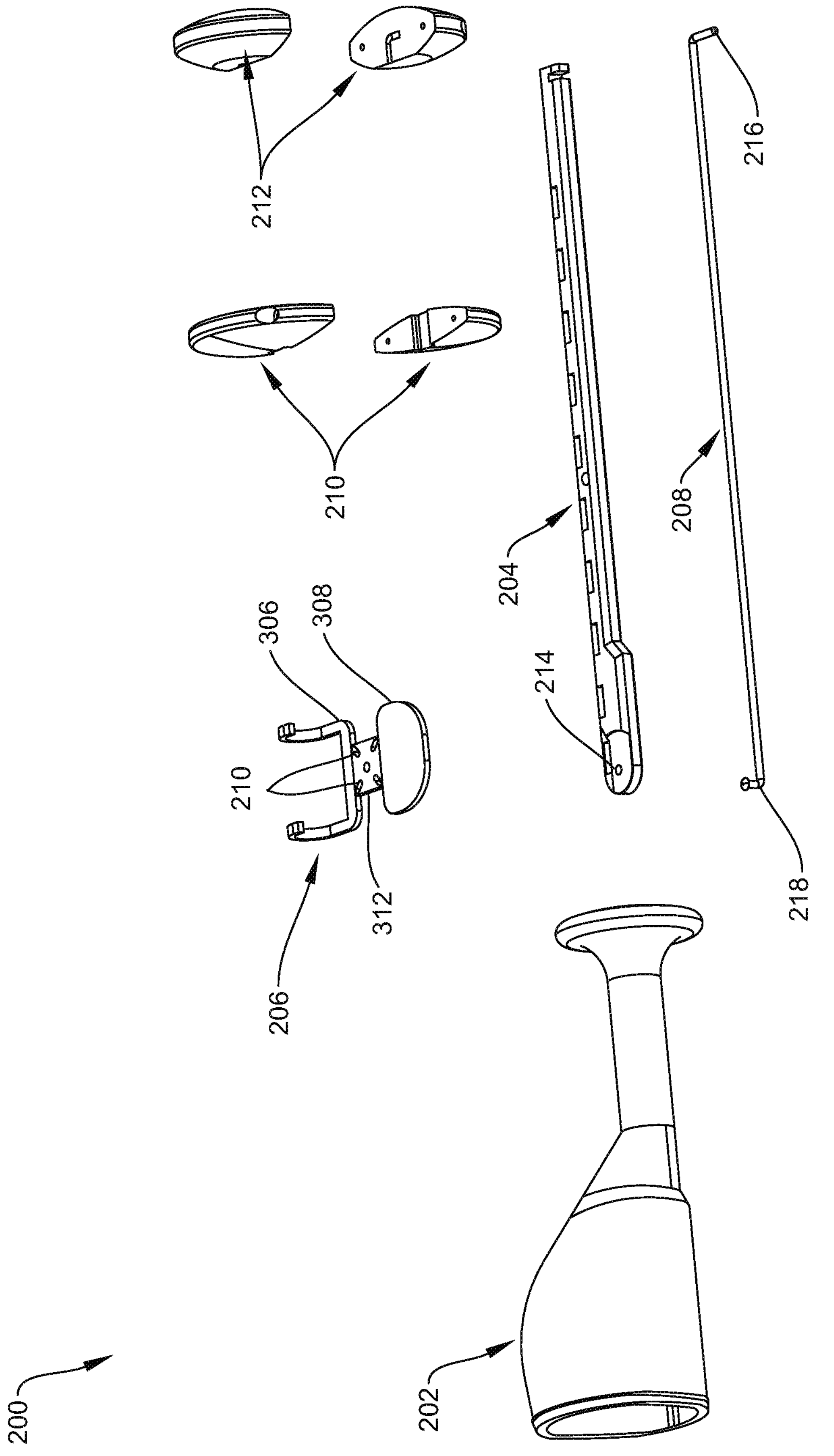
FIG. 2 depicts an exploded view of a pessary insertion apparatus, in accordance with the disclosed subject matter.

Referring now to FIG. 2, with additional reference to FIGS. 3A-5B, various views of a pessary insertion apparatus 200 are shown. As shown in FIG. 2, one embodiment of the apparatus may include a body 202, a support member 204, a pessary-engaging structure 206, a rod 208, a handle 210, and an actuator 212. The pessary-engaging structure 206 can include multiple arms (e.g., a first arm 306 and a second arm 308) coupled to or extending from a middle member 312.

In some embodiments, the pessary insertion apparatus is provided in multiple size variants. The overall dimensions of one or more components, such as the body 202, the support member 204, or the pessary-engaging structure 206 (including the arms 306, 308), can differ between the size variants. Each size variant can be selected for use with a corresponding subset of standard pessary sizes. For example, a "small," "medium," or "large" apparatus size can be configured to engage and deploy ring pessaries and ring pessaries with a bulge having outer diameters within predetermined ranges (e.g., about 44 mm to about 64 mm, about 57 mm to about 89 mm, or about 83 mm to about 127 mm). In many embodiments, for example wherein the apparatus sizes are provided as "small," "medium," or "large" the small may be configured to accept pessary sizes 3-5, the "medium" to accept 5-6, and the "large" to accept 6-8, which sizes may accommodate ~85% of users The support member 204 of the present embodiment defines an internal channel extending along its longitudinal axis, the channel being dimensioned to receive and guide the rod 208 during translation. In some embodiments, the support member 204 does not define an internal channel, and the rod 208 is disposed along an exterior surface of the support member 204. In such embodiments, one or more guide features (e.g., rails, clips, sleeves, recessed path) can be formed or coupled to the support member 204 to maintain axial alignment of the rod and permit its longitudinal translation.

The body 202 can be formed as a rigid or semi-rigid structure selected to provide structural stability for insertion and manipulation while maintaining a comfortable profile for the user. The support member 204 can also be formed of a rigid material selected to maintain a stable connection with the body 202 and the pessary-engaging structure 206.

The pessary-engaging structure 206 can be formed of a flexible or elastomeric material selected to permit repeated folding, bending, or deformation, and subsequent return to its original shape. The materials for the pessary-engaging structure 206 can be selected to provide user comfort and biocompatibility. The flexibility of the pessary-engaging structure 206 can allow the structure to temporarily retain the pessary device while minimizing discomfort during deployment by reducing localized pressure against the surrounding vaginal tissue. In particular, the pessary-engaging structure 206 can deflect under a load, distribute contact forces over an area, and/or reduce frictional resistance between the structure and vaginal tissue.

The geometry and material of the arms of the pessary-engaging structure 206 can enable the structure to accommodate different ring diameters and thicknesses. In some embodiments, the pessary-engaging structure 206 accommodates a selected subset of standard pessary sizes (e.g., standard pessary sizes 2 through 7). In some embodiments, the pessary-engaging structure 206 is configured to engage pessary devices having outer diameters in a range of about 44 mm to about 64 mm. In some embodiments, the pessary-engaging structure 206 is configured to engage pessary devices having outer diameters in a range of about 57 mm to about 89 mm. In some embodiments, the pessary-engaging structure 206 is configured to engage pessary devices having outer diameters in a range of about 83 mm to about 127 mm. In some embodiments, the pessary-engaging structure 206 is configured to engage a specific pessary size, such as a ring pessary having an outer diameter of about 44 mm, about 51 mm, about 57 mm, about 64 mm, about 70 mm, about 76 mm, about 83 mm, about 89 mm, about 95 mm, about 102 mm, about 108 mm, about 114 mm, about 121 mm, or about 127 mm. The particular range or specific size accommodated by a given pessary-engaging structure 206 can vary depending on the geometry and stiffness of the arms.

In some embodiments, compliant arm geometry provides passive sizing (without adjustment). In other embodiments, adjustable arms, interchangeable arms sets and/or other adjustable features provide selectable and/or active sizing while maintaining the ability to releasably retain the device during loading and deployment.

In some embodiments, the pessary-engaging structure 206 is provided in multiple size variants, each variant having dimensions selected for a corresponding ring diameter or range of ring diameters. The support member 204 can include an attachment interface 214, such as a snap-fit, keyed, threaded, or press-fit connection, that can allow different pessary-engaging structures to be attached to/detached from the support member 204 and/or rotate around a central axis.

In some embodiments, the arms of the pessary-engaging structure include one or more adjustable features, such as elastomeric ribs (as shown in FIG. 2), that can deform to accommodate different pessary devices. The use of arms with elastomeric features can allow a single pessary-engaging structure to adapt to multiple pessary sizes without replacement. While FIG. 2 and subsequent figures show these elastomeric features one arm (i.e. arm 306) both arms may include elastomeric features of the same or similar shape. While the elastomeric features shown in the present figures are "u" shaped, other configurations may be used.

In some embodiments, the arms of the pessary-engaging structure (e.g., the first arm 306 and second arm 308) are detachably coupled to the middle member 312 and may pivot with the middle member 312 about a central axis. For example, the middle member 312 can define one or more arm-receiving interfaces, such as hinge-pin feature, pin-and-socket feature, keyed slots, dovetail tracks, or snap-fit sockets, that can allow the arms to be removably attached while maintaining a stable pivotable connection during use. In this configuration, different arms sets can be interchanged to accommodate different pessary sizes or ring profiles. In some embodiments, multiple sets of arms can be provided, such as arms having different radii of curvature, planar arms having different surface areas, and/or arms having different stiffness. In other embodiments, the arms and middle member may be removed and replaced as a single unit to alter the radius and size of the pessary-engaging structure—for example to aid in accommodating pessary devices of different sizes and/or shapes.

The handle can be formed as a single molded piece or from multiple components coupled together. As shown in FIG. 2, the handle 210 can include a recess configured to receive an end of the support member 204 and a groove through which the rod 208 can extend.

The actuator 212 can also be formed as a single molded piece or from multiple components coupled together. In some embodiments, the actuator 212 is sized and shaped to function as a second handle (e.g., lever, slider) during operation of the apparatus 200. For example, the actuator 212 can define one or more gripping surfaces, contours, or flanges sized to be grasped by a user. In some embodiments, the actuator 212 is configured as a thumb-press or a trigger.

The actuator can include a rod retaining feature (e.g., a groove) configured to operatively engage the rod 208 so that movement of the actuator 212 causes corresponding movement of the rod 208. In some embodiments, the actuator 212 includes a groove, a slot, or a notch configured to receive and retain a first end 216 of the rod 208 such that movement of the actuator 212 causes translation of the rod 208 relative to the support member 204. The groove geometry can vary; for example, it can be straight, L-shaped, or U-shaped. The rod end can be secured to the rod retaining feature by a press-fit, snap-fit, sliding engagement, keyed engagement, or threaded engagement. In some embodiments, the rod 208 and actuator 212 include interlocking or complementary surfaces that prevent axial disengagement while still allowing the rod 208 to translate longitudinally within the channel of the support member 204, when the actuator 212 is operated.

The opposing, second end 218 of the rod 208 can be received through an opening in the support member 204 and into an opening or coupling interface of the middle member 312 of the pessary-engaging structure 206. This configuration permits the linear translation of the rod 208 to be transferred to the middle member 312, as described in further detail with respect to FIGS. 3B and 5A-5B.

Figure 3A:
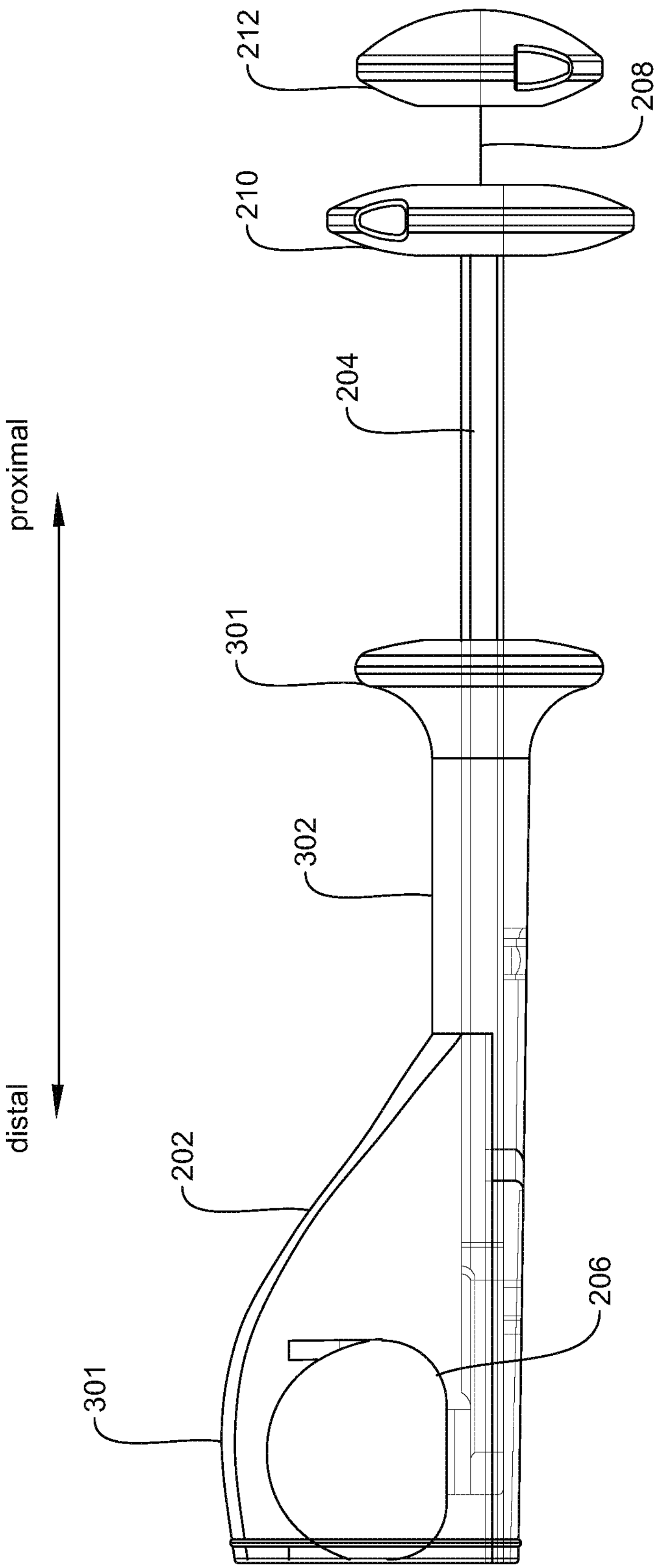
FIG. 3A depicts a side view of a pessary insertion apparatus as shown in FIG. 2, in accordance with the disclosed subject matter.

Referring now to FIG. 3A, a side view of the pessary insertion apparatus 200 is shown with the pessary-engaging structure 206 in a collapsed configuration and positioned within the body 202 (between a first end and a second end of the body). The body 202 includes a first (proximal) end positioned toward the handle 210 and a second (distal) end positioned away from the handle. The support member 204 is disposed at least partially within the interior of the body 202 and extends along a longitudinal axis of the apparatus.

The first arm 306 and the second arm 308 of the pessary-engaging structure 206 can be positioned on either lateral side of the middle member 312 when the pessary-engaging structure 206 is in the collapsed configuration (see e.g., FIG. 3A). Lateral side refers to locations that are offset from a longitudinal midline extending axially through the support member 204 and the middle member 312.

The lateral placement of the arms 306, 308 of the pessary-engaging structure 206 can determine which direction the pessary-engaging structure 206 rotates during actuation. Rotation of the pessary-engaging structure 206 can occur in a clockwise or counterclockwise direction to position the first arm 306 adjacent to the interior of the body 202 and the planar arm 308 toward the anatomical placement region (e.g., fornix).

The body 202 can be formed as a single, integral structure or as multiple coupled components (e.g., distal and proximal portions that are permanently bonded or mechanically coupled together). In some embodiments, the body 202 defines two or more longitudinal portions having different outer profiles. For example, as shown, the body 202 can include a first portion 301 adjacent the second end of the body, an intermediate second portion 302, and a third portion 303 positioned adjacent the first end of the body. The portions 301, 302, and 303 can differ in cross-sectional area, taper, contour, or texture. For example, the first portion 301 can include a taper or a curved transition sized to facilitate insertion and to allow the interior of the body 202 to surround the pessary engaging-structure 206 when the apparatus is in the loaded configuration. The second portion 302 can have a circular, rectangular, or another cross-sectional profile suitable for guiding translation of the support member 204. The third portion 303 can be tapered, contoured, or otherwise shaped to function as a gripping region that a user can grasp to translate the body 202 relative to the support member 204. In some embodiments, the third portion 303 includes surface texturing (e.g., ribs, grooves, or surface relief) to improve tactile control.

Transitions between portions of the body 202 can be linear, curved, radiused, parabolic, stepped, filleted, or compound. The geometry of each portion can be selected to balance insertion comfort, manufacturability, tactile feedback, and structural support.

External contours of the body 202 and the exposed edges of the pessary-engaging structure 206 can be formed with radiused or otherwise curved profiles and without sharp edges. Curved profiles can reduce stress concentrations, minimize snagging or abrasion on tissue or on a folded pessary device and improve user comfort during insertion and manipulation, particularly for those portions that contact or are proximate to tissue.

The body 202 can define a first opening at the first end of the body and a second opening at the second end of the body, the second opening having a larger area than the first opening. In such embodiments, the pessary device can be introduced into the body 202 through the second opening (e.g., larger opening).

The first end of the support member 204 can be coupled (e.g., threadably coupled) to the handle 210, such that the handle 210 provides a stabilization and gripping structure during use. The second end of the support member 204 can be coupled to the pessary-engaging structure 206. In the loaded configuration, a portion of the support member 204 can project proximally beyond the first end of the body 202, defining a translation distance through which the body 202 can be drawn proximally toward the handle 210 to expose the pessary-engaging structure 206 through the second end of the body during deployment.

Figure 3B:
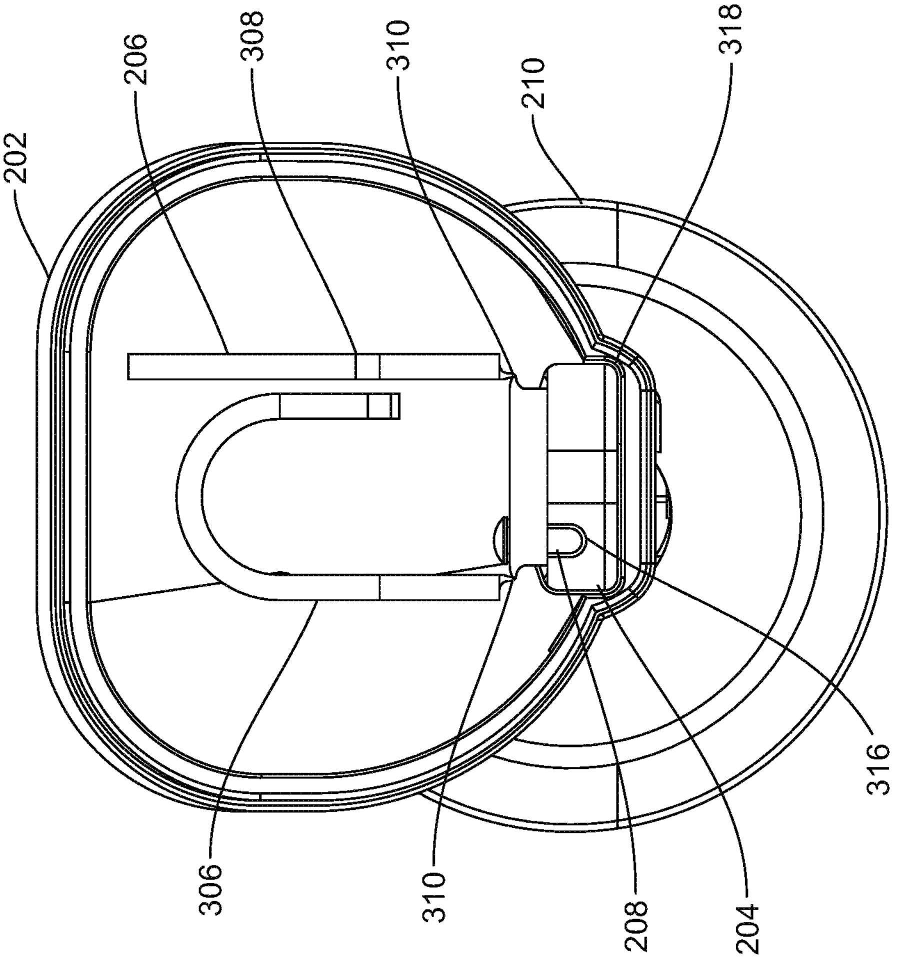
FIG. 3B depicts a front view of a pessary insertion apparatus as shown in FIG. 2, in accordance with the disclosed subject matter.

Referring now to FIG. 3B, a front view of pessary insertion apparatus is shown, with the pessary-engaging structure 206 in a collapsed configuration and positioned within the interior of the body 202. As shown in FIG. 3B, the pessary-engaging structure 206 can include a middle member 312 coupled to the second end of the support member 204, and multiple arms (e.g., a first arm 306 and a second arm 308) coupled to the middle member 312.

The pessary-engaging structure 206 can include a first arm 306 having one or more elastomeric, curved, and/or rib-shaped portions and a second arm 308 having a planar surface, each arm extending from the middle member 312. The one or more curved portions can define a receiving region sized and shaped to releasably retain a portion of a folded pessary device (without permanently clamping or locking). The receiving region can have a concave or cradle-like geometry that conforms to the outer ring 102 of the pessary device. The planar surface of the second arm 308 can provide counter support to the pessary device, stabilizing an opposite portion of the ring during insertion, rotation, and release.

In most embodiments, the second arm 308 does not extend beyond the outer diameter of the pessary device and instead terminates inside of the pessary device's outer profile, this may aid in lessening the extent of contact between the second arm and vaginal tissue. In some embodiments, the second arm 308 may be flush with, or extends beyond the outer diameter of a pessary device positioned within the pessary-engaging structure 206.

The receiving region is configured to aid in releasably retaining the pessary device both when the pessary-engaging structure 206 is in a collapsed configuration (e.g., within the body 202 in the loaded configuration) and when the structure is in an expanded configuration (e.g., outside of the body 202). Release of the pessary device from the pessary-engaging structure may occur upon positioning at or near its intended placement location (e.g. near the fornix). In some embodiments, the user may apply a slight retraction, offset, or reduction in contact pressure to aid positioning.

Figure 8A:
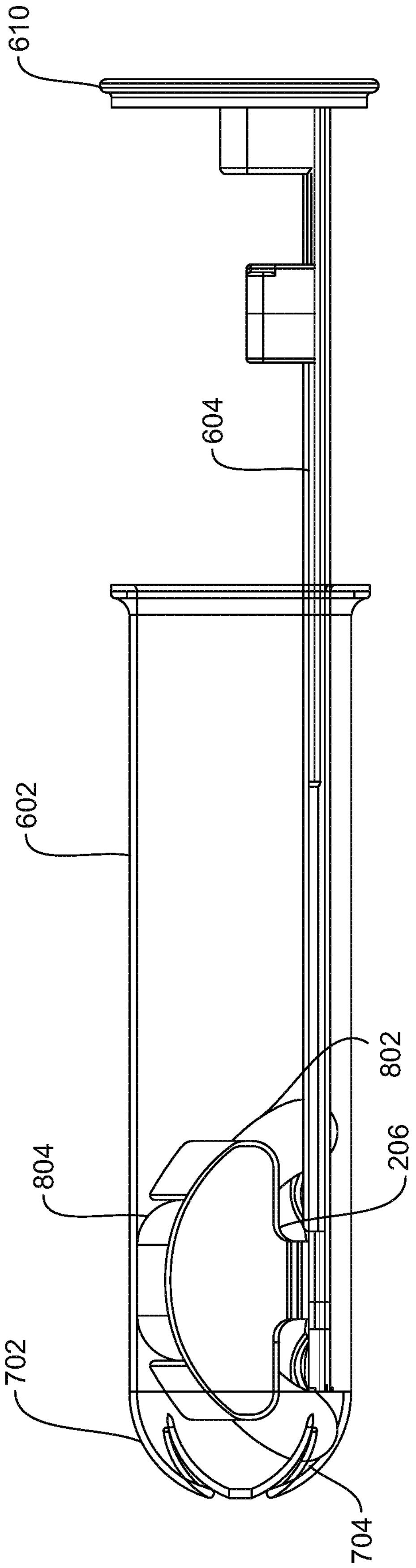
FIG. 8A depicts a side view of a pessary insertion apparatus holding a pessary device in a folded configuration and with the apparatus in a loaded configuration, in accordance with the disclosed subject matter.
Figure 8B:
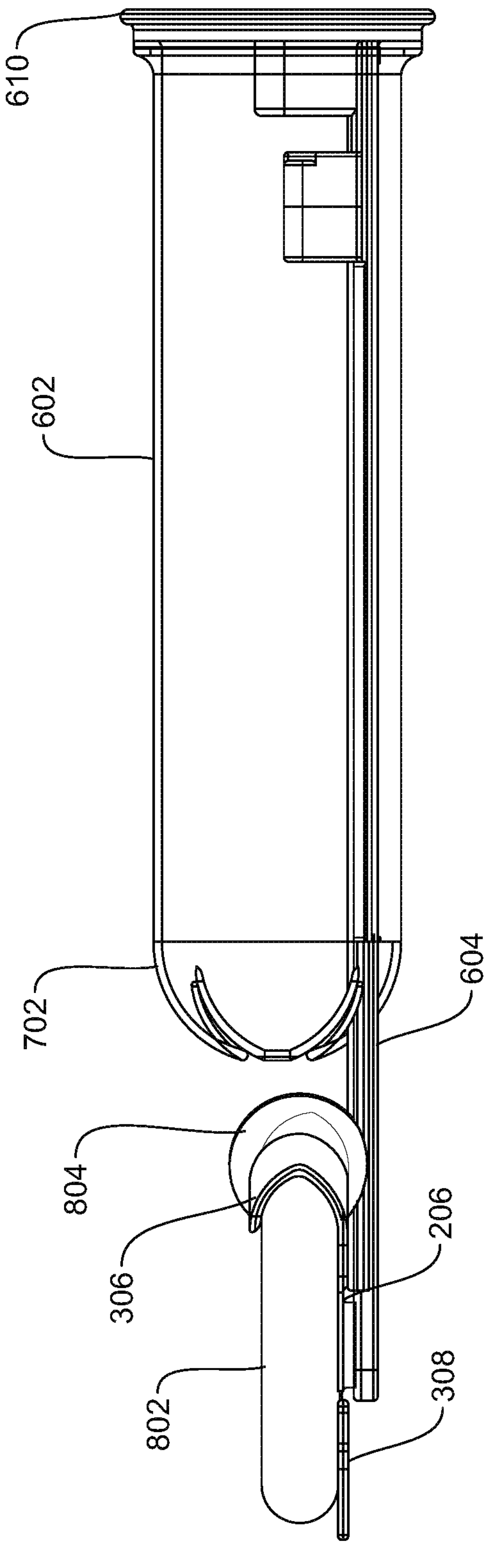
FIGS. 8B-8C depict top views of a pessary insertion apparatus holding a pessary device with the apparatus in a deployed configuration, in accordance with the disclosed subject matter.
Figure 8C:
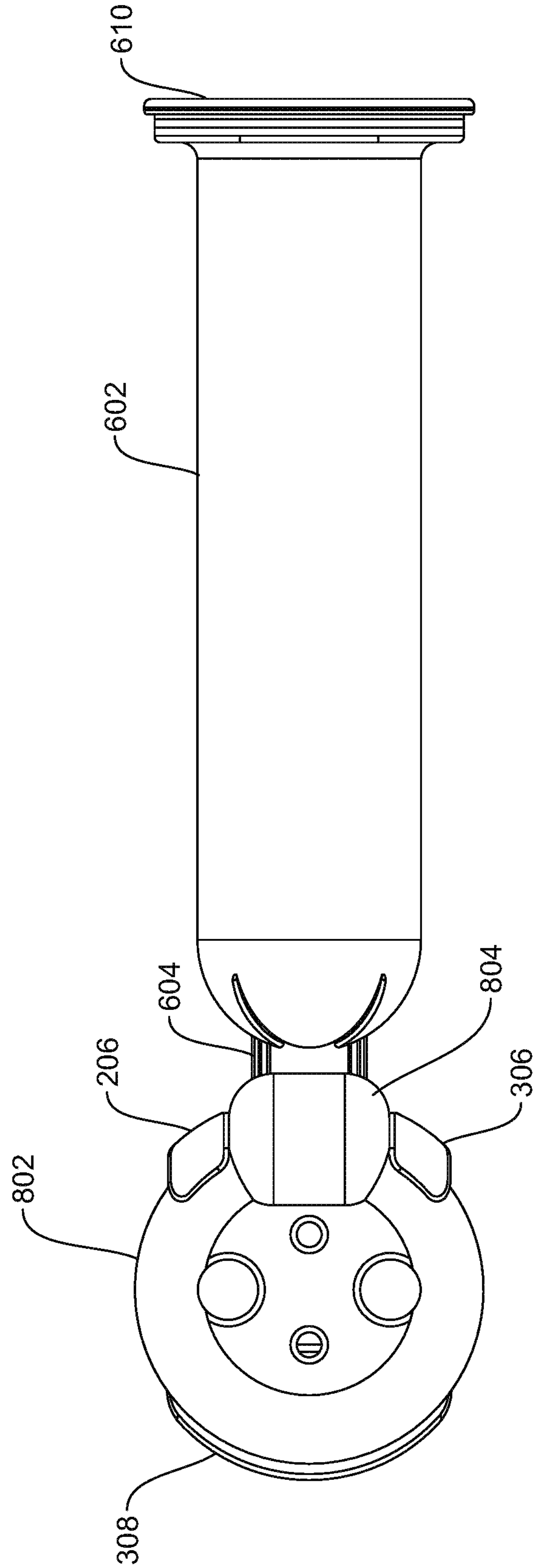

In some embodiments in which the pessary device is a ring pessary having a bulge (e.g., bulge 108), the bulge can be positioned between the two curved or rib-shaped portions of the first arm 306 of the pessary-engaging structure (see e.g., FIGS. 8A-8C). In such embodiments, the bulge can reside within the receiving region defined by the curved portions, which can stabilize the folded pessary device and inhibit lateral shifting while the pessary-engaging structure is positioned within the body 202 in the loaded configuration and during deployment while positioning the device in the vagina.

In some embodiments, the receiving region of the first arm 306 may be sized to accommodate ring pessaries without a bulge or other disk- or ring-shaped pessaries, and the curved geometry can be selected to stabilize the device independent of the presence or absence of a bulge. As noted above, in some embodiments the two arms of the pessary-engaging structure may comprise curved or rib-shaped structures that may aid in retaining, deploying, and/or positioning the pessary device.

In some embodiments, the pessary device is folded prior to engagement with the pessary-engaging structure; in other embodiments, the pessary device is positioned between the arms in an unfolded configuration, and the arms are then pivoted inward to fold or partially fold the pessary device while it is held by the pessary-engaging structure 206. When a folded pessary device is engaged with the arms 306, 308, the pessary device stores elastic restoring force due to its deformation. In the loaded configuration, the body 202 at least partially surrounds the pessary-engaging structure 206 and thereby constrains the arms, preventing the pessary device from returning to its unfolded configuration. Upon translation of the body 202 proximally relative to the support member 204, the pessary-engaging structure 206 becomes exposed through the second end of the body 202, and the restoring force of the pessary device urges the arms outward, returning the pessary-engaging structure 206 toward an expanded configuration. In some embodiments, the pessary-engaging structure 206 itself exhibits a restoring force, such that expansion may be driven by the pessary device, the structure 206, or a combination thereof.

The arms 306, 308 of the pessary-engaging structure 206 can be joined to the middle member 312 by a living hinge 310, allowing the arms to pivot toward and away from one another while remaining integrally connected to the middle member 312. In the collapsed configuration, the first arm 306 and second arm 308 of the pessary-engaging structure 206 pivot inward about their respective living hinges, thereby reducing the span of the structure so that it is retained within the interior of the body 202. The arms 306, 308 and the living hinges 310 can be formed from a soft or compliant material, such as silicone, thermoplastic elastomer, thermoplastic polyurethane, latex-free elastomer, or medical-grade rubber. This compliant construction can allow the arms to conform to the curvature of a folded pessary device and can reduce localized pressure during retention and deployment. Rounded edges or radiused transitions between the arms and the middle member can further reduce tissue abrasion, minimize snagging during insertion or withdrawal, and improve user comfort. In some embodiments, the arms 306, 308 are not integrally formed with the middle member 312 and the pessary-engaging structure 206 is formed of two or more distinct components (e.g., three components). The arms 306, 308 can be separately manufactured components coupled to the middle member 312 by a pivoting joint such as a micro-piano hinge, a snap hinge, a pin-and-socket hinge, or another mechanical pivot feature that allows the arms to fold toward and away from one another.

Figure 4A:
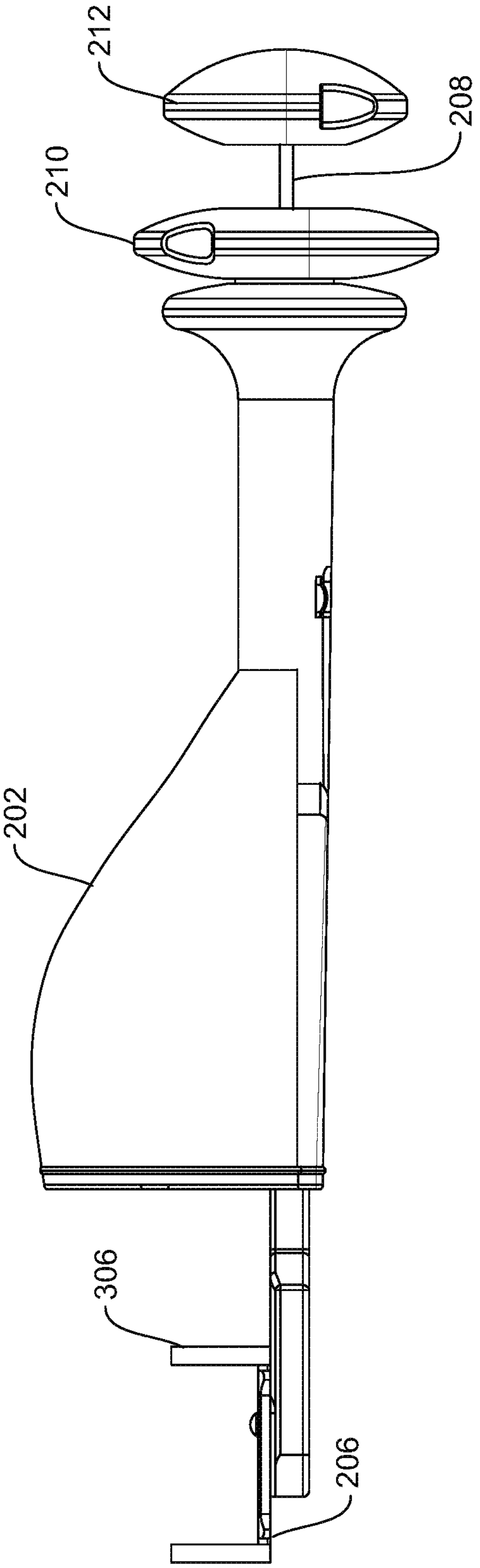
FIG. 4A depicts a side view of a pessary insertion apparatus, as shown in FIG. 2, with a pessary-engaging structure positioned outside of the body of the apparatus, in accordance with the disclosed subject matter.
Figure 4B:
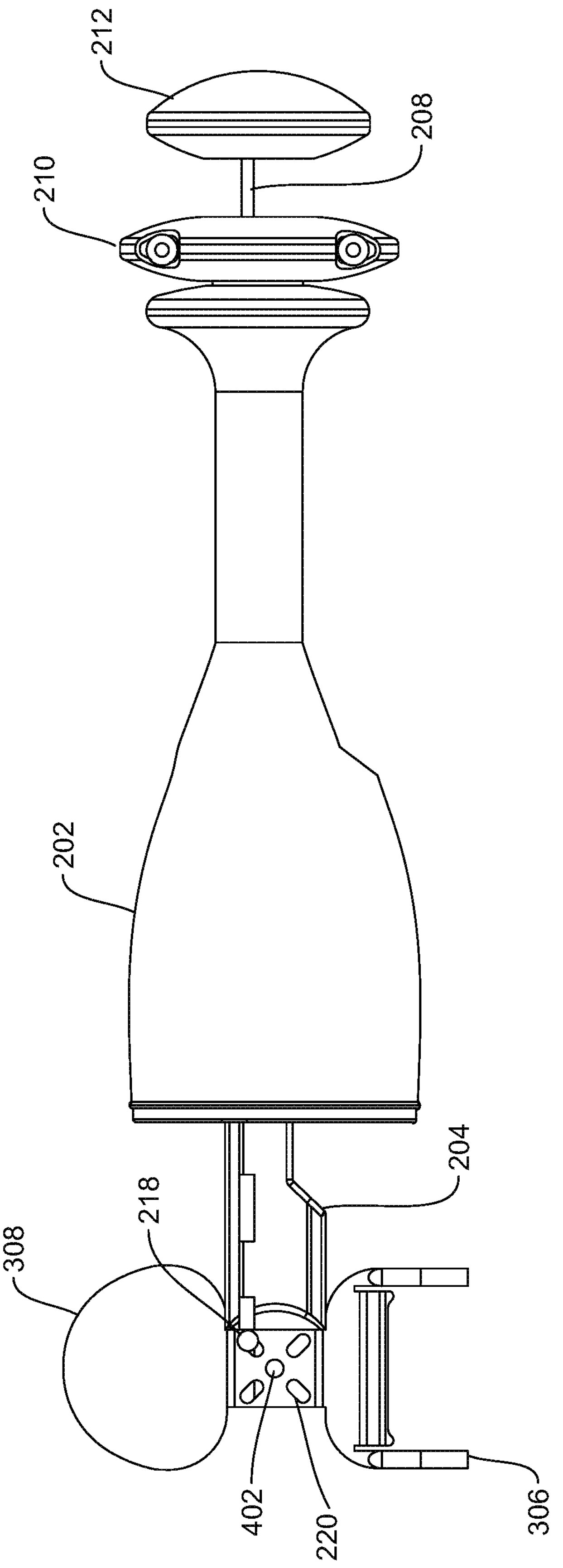
FIG. 4B depicts a top view of a pessary insertion apparatus, as shown in FIG. 2, with a pessary-engaging structure positioned outside of the body of the apparatus, in accordance with the disclosed subject matter.

The middle member 312 can be planar and can define multiple openings 220 (e.g., as shown in FIG. 2 and FIG. 4B) to reduce material volume, improve flexibility, or interface with the rod 208 or support member 204. For example, the middle member 312 can define two, three, four, or more openings, and may be circular, polygonal, rectangular, oval, or contoured. Any one of the openings of the middle member 312 can receive or engage the second end 218 of the rod 208. The middle member 312 can be mounted on a surface of the support member 204 such that the pessary-engaging structure 206 remains on the support member 204 during loading, manipulation, and deployment, while still being rotatable relative to the support member 204.

The position at which the second end 218 of the rod 208 engages one of the openings of the middle member 312 can influence operation of the apparatus. For example, depending on which opening 220 receives the second end 218 of the rod 208, the pessary-engaging structure 206 may rotate in a clockwise or counterclockwise direction when the actuator 212 is operated. In some embodiments, the selected opening also affects the direction in which the actuator 212 is moved (e.g., pushed or pulled) to transition the pessary-engaging structure 206 between the collapsed and deployed configuration. Additionally, the location of rod engagement can influence the extent of available angular rotation and the amount of linear rod translation required to achieve complete deployment or retraction (of the structure 206 into the body 202 following deployment).

The rod 208 can be coupled to the middle member 312 at an offset location such that translation of the rod 208 applies a rotational moment to the middle member 312, thereby rotating the pessary-engaging structure 206 about a rotation axis that extends perpendicular to the longitudinal axis of the support member 204. In FIG. 3B, a second end 218 of the rod (e.g., second rod end) extends from the channel 316 the support member 204 and through a thickness of the middle member (at an offset location).

As shown in FIG. 3B, the channel 316 extending longitudinally through the support member 204 is not centered within the cross-section of the support member 204. Instead, the channel 316 is offset from a central longitudinal axis of the support member by a distance. In some embodiments, the support member 204 has a rectangular or non-circular cross-section, and the channel 316 is positioned closer to one side of the cross-section. In some embodiments, the support member 204 has a circular or oval cross-section, and the channel is located at a radial position relative to the central longitudinal axis. The offset can be measured from the longitudinal axis of the support member 204 to the axis of the channel 316.

Positioning the channel in an off-axis location can provide a mechanical advantage when the rod 208 is translated, producing an unbalanced moment that induces rotation of the pessary-engaging structure 206 when the pessary-engaging structure 206 is in an expanded configuration. The actuator-and-rod assembly therefore functions as a linear-to-rotational conversion mechanism, in which linear displacement of the rod is transformed into angular displacement of the pessary-engaging structure 206. Other rotation-inducing mechanisms can be used in alternative embodiments. For example, the rod 208 can be configured to rotate about its longitudinal axis rather than translate linearly, and the second end 218 of the rod 208 can operably interface with a gear train, cam system, or other motion-conversion interface configured to rotate the pessary-engaging structure 206.

The body 202 can define a guide channel 318 configured to guide translation of the body 202 relative to the support member 204. In some embodiments, the guide channel 318 is formed as a longitudinal recess, slot, or track along an interior surface of the body 202 that receives at least a portion of the support member 204 and constrains its motion. The guide channel 318 can include raised ribs, slide rails, bushings, or bearing surfaces that maintain axial alignment between the body 202 and the support member 204 while permitting translation during loading and deployment.

Referring now to FIG. 4A, a side view of the pessary insertion apparatus 200 is shown in a partially deployed configuration, in which the pessary-engaging structure 206 has been translated beyond the second end of the body 202 but has not yet been rotated. In this configuration, the arms of the pessary-engaging structure 206 can expand from the collapsed configuration due to release of constraint by the body 202 and, in some implementations, due to restoring force stored in a folded pessary device positioned between the arms.

Referring now to FIG. 4B, a top view of the pessary-engaging structure 206 is shown in which a pivot feature 402 and the second rod end 218 are visible. The middle member 312 of the pessary-engaging structure 206 can be coupled to the second end of the support member 204 via the pivot feature 402, which can include a pin. The pivot feature 402 prevents axial separation of the pessary-engaging structure 206 from the support member 204 while permitting rotation of the pessary-engaging structure 206 about a rotation axis extending perpendicular to the longitudinal axis of the support member 204.

In some embodiments, the rotational coupling between the middle member 312 and the support member 204 is provided by an offset hinge or pivot feature rather than the centered pivot feature shown in the present figures. For example, the pessary-engaging structure 206 can be coupled to the support member 204 by a living hinge, micro-piano hinge, snap hinge, or other hinge element configured to permit rotation about an axis while maintaining attachment. The hinge feature can be positioned on a side of the middle member 312.

Figure 5A:
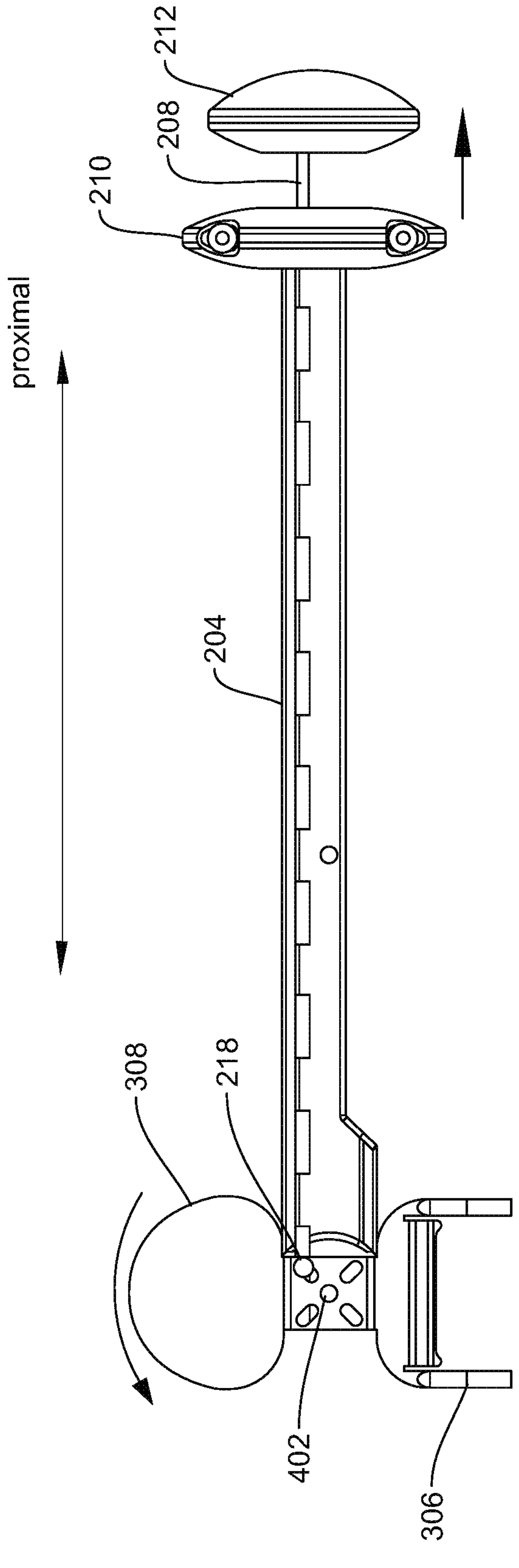
FIGS. 5A-5B depict top views illustrating a sequence of rotation of the pessary-engaging structure and associated actuation components of the pessary insertion apparatus in response to actuation, in accordance with the disclosed subject matter. For clarity, the body of the apparatus is omitted in these views.
Figure 5B:
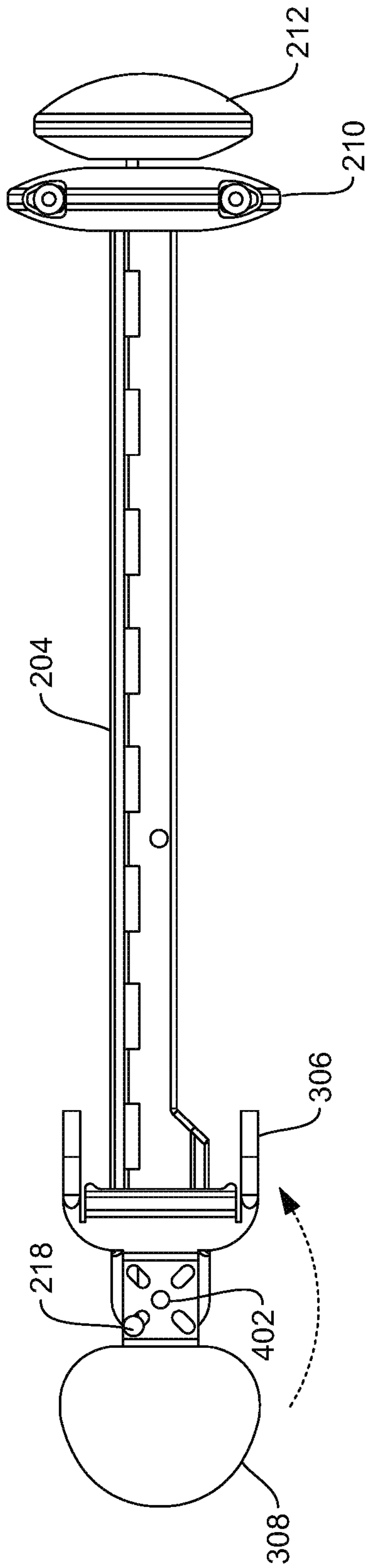

Referring now to FIGS. 5A and 5B, top views of the pessary-engaging structure 206 are shown, with the body 202 omitted for clarity. The pessary-engaging structure 206 is mounted to the support member 204 at a middle member 312, which is coupled to the support member 204 by a pivot feature 402 defining a rotation axis generally transverse to the longitudinal axis of the support member 204. The second end 218 of the rod 208 engages the middle member 312 at a location offset from the rotation axis, such that translation of the rod 208 generates a rotational moment.

Because the second end 218 of the rod 208 is spaced from the pivot axis, translation of the rod 208 relative to the support member 204 applies a rotational moment to the middle member 312, thereby rotating the pessary-engaging structure 206 between a first angular orientation (FIG. 5A) and a second angular orientation (FIG. 5B) suitable for positioning the pessary device. In some embodiments, the rotational range is about 450 to about 120°. In some embodiments, the rotational range is about 90°.

In the partially deployed configuration, a segment of the rod 208 is exposed between the actuator 212 and the handle 210, indicating available travel. The actuator 212 is operatively coupled to the rod 208 such that driving the actuator 212 towards the handle 210 translates the rod 208 within the channel of the support member 204, rotating the pessary-engaging structure from the first angular orientation toward the second angular orientation. The rotation of the pessary-engaging structure 206 can occur in either a clockwise or a counterclockwise direction about the pivot axis (e.g., depending on the geometry of the coupling between the rod 208 and the middle member 312).

In some embodiments, the middle member 312 additionally allows limited out-of-plane angulation of the pessary-engaging structure 206, for example tilting by about 100 to about 300 about a secondary axis. For example, in addition to rotation about the primary axis, defined by the pivot feature 402, the pessary-engaging structure 206 can tilt about a secondary axis that is non-parallel to the primary rotation axis. The secondary axis can be orthogonal to both the longitudinal axis of the support member 204 and the primary rotation axis. Such controlled angulation can facilitate release and/or positioning of the pessary device within the vaginal canal after placement at or near the fornix of the vagina, while still maintaining secure engagement during loading of the device onto the apparatus and insertion of the apparatus into the vagina.

In some embodiments, the out-of-plane angulation is facilitated by user manipulation of the apparatus. For example, the user can tilt or angle the handle 210 relative to the initial insertion orientation of the apparatus, which can cause the pessary-engaging structure 206 to tilt about the secondary axis.

In some embodiments, the apparatus includes structural features that promote the out-of-plane angulation. For example, the support member 204 can include a ramped or contoured surface adjacent to the pessary-engaging structure 206 such that, as the structure rotates about the primary axis, a portion of the pessary device contacts the ramped surface and is thereby urged upward to produce the secondary-axis tilt.

In some embodiments, the geometry of the pessary device contributes to the angulation. For example, when deploying a ring pessary device with a bulge, rotation of the pessary-engaging structure 206 can result in the bulge resting on a surface of the support member 204 after rotation (e.g., as shown in FIG. 8B). Because the bulge has a greater thickness than adjacent portions of the ring, its contact with the support member 204 can cause the pessary-engaging structure 206 to angle about the secondary axis.

Figure 6:
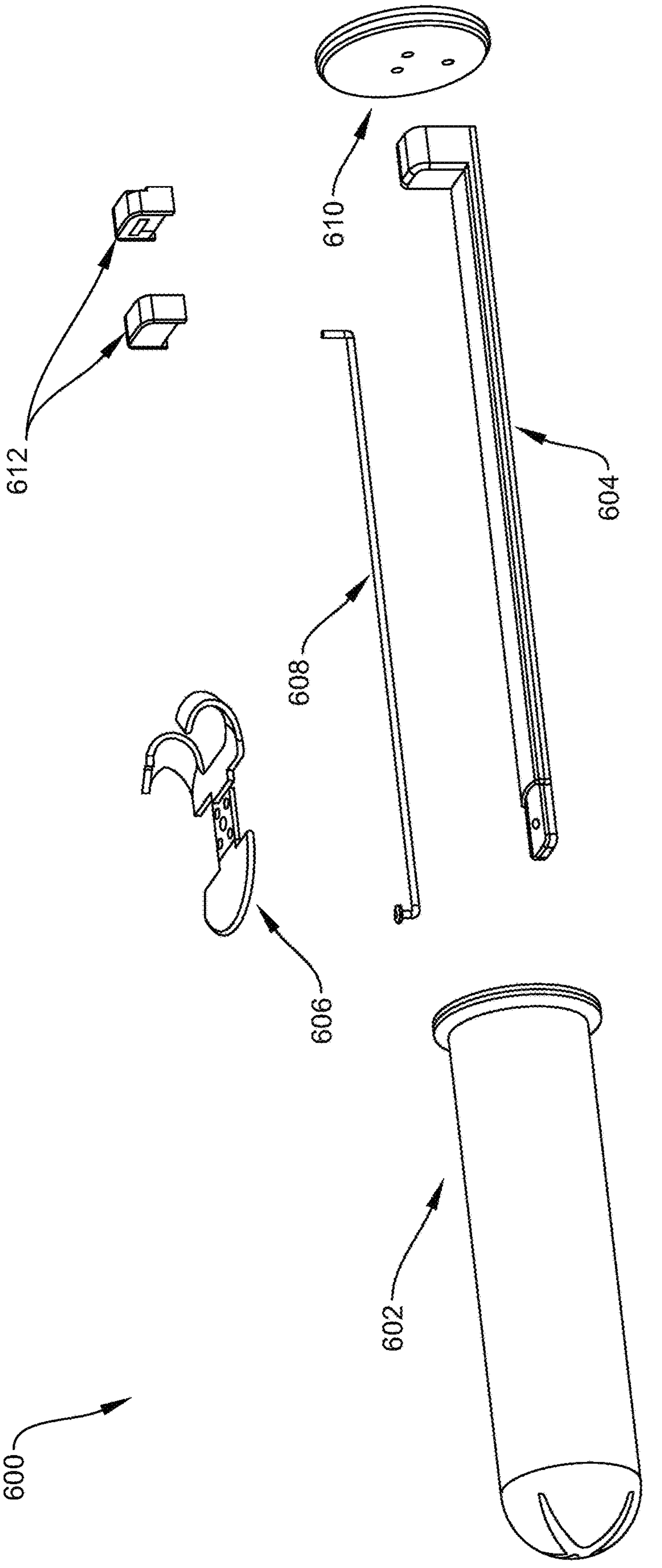
FIG. 6 depicts an exploded view of another embodiment of the pessary insertion apparatus, in accordance with the disclosed subject matter.
Figure 7A:
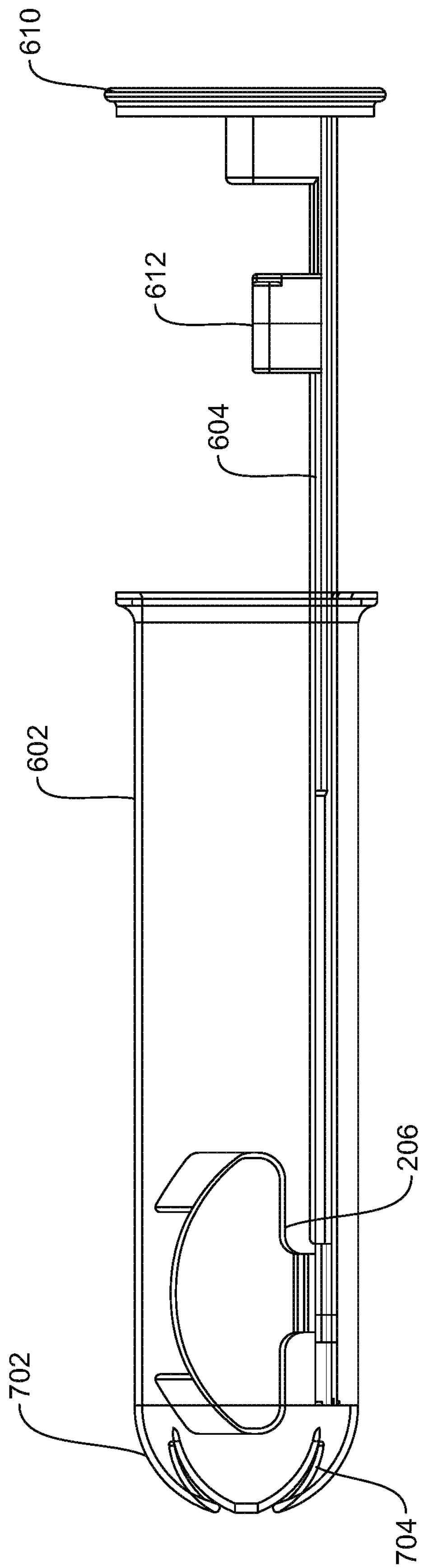
FIG. 7A depicts a side view of a pessary insertion apparatus, as shown in FIG. 6, with a pessary-engaging structure positioned within the body of the apparatus, in accordance with the disclosed subject matter.

Referring now to FIG. 6, with added reference to FIG. 7A, an exploded view and a side view of a pessary insertion apparatus 600 is shown. The apparatus 600 includes a body 602, a support member 604 configured to be disposed at least partially within the body 602, a pessary-engaging structure 206 coupled to a second (distal) end of the support member 604, a rod 208 positioned within a channel extending along the support member 604, a handle 610 at a first (proximal) end of the support member 604, and an actuator 612 operatively coupled to the rod 208.

The body 602 can be cylindrical and can include a cap 702 at the second end of the body. The cap 702 can be rounded, semi-spherical, dome-shaped, tapered, or otherwise smoothly contoured to facilitate insertion. The cap 702 can include one or more slits 704 that define compliant flaps that flex as the pessary-engaging structure 206 moves through the second end of the body 602. The cap 702 can be formed of a flexible material such as silicone, thermoplastic elastomer, polyurethane, medical-grade rubber, or combinations thereof. The cap 702 can be integral with the body 602 or can be removably coupled to allow loading of a pessary device from the second end of the body 602. In some embodiments, the body 602 includes a proximal flange configured to provide a grasping surface for stabilizing the apparatus during use.

The actuator 612 is positioned along the support member 604 (e.g., proximal to the handle 610). The support member 604 can include a slot, opening, or window through which a portion of a first end of the rod 208 extends to operatively engage the actuator 612. In some embodiments, the first end of the rod 208 is directly connected to the actuator 612.

In some embodiments, the body 602 includes an internal engagement surface, ledge, cam, ramp, or follower surface configured to contact and advance the actuator 612 when the body 602 is translated relative to the support member 604. Translation of the body 602 therefore drives translation of the actuator 612 along the support member 604, which in turn translates the rod 208 within the channel and rotates the pessary-engaging structure 206. Because exposure and rotation occur during the same motion, the apparatus 600 can be operated as a single-step deployment device, reducing the number of user steps needed to place the pessary device within the vaginal canal. Translation of the rod 208 rotates the pessary-engaging structure 206 as described with respect to FIGS. 9A-9B.

In the two-step embodiment (e.g., apparatus 200), the body is translated relative to the support member to expose the pessary-engaging structure, and the actuator is thereafter actuated to rotate the structure. In the one-step embodiment (e.g., apparatus 600), translation of the body relative to the support member both exposes and rotates the pessary-engaging structure in one continuous motion.

Figure 7B:
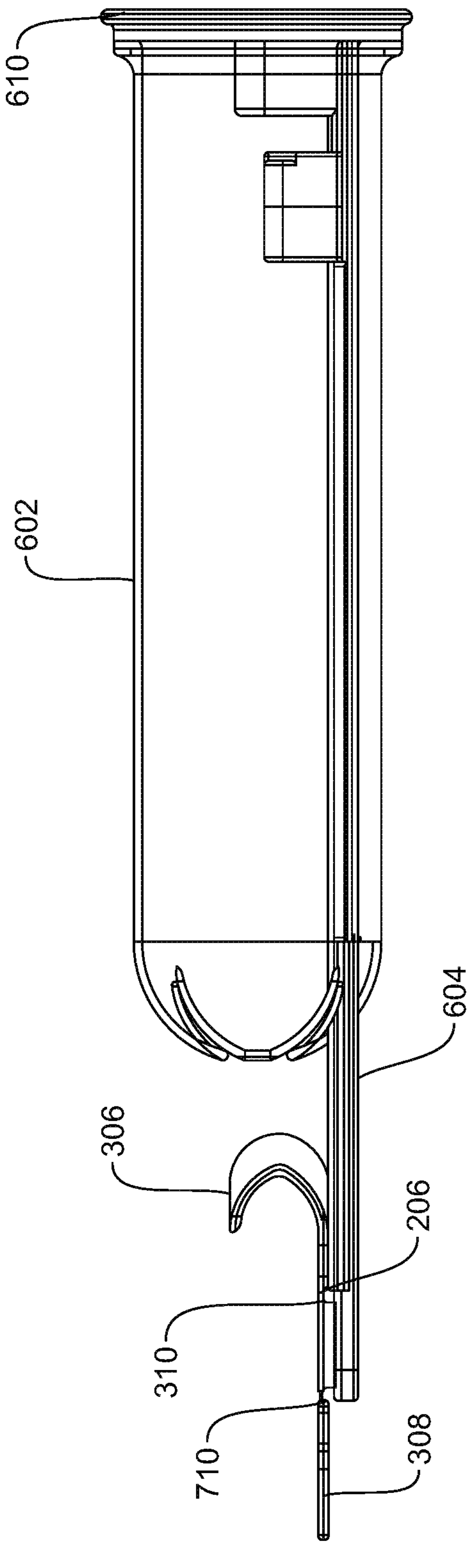
FIG. 7B depicts a side view of a pessary insertion apparatus, as shown in FIG. 6, with a pessary-engaging structure positioned outside of the body of the apparatus, in accordance with the disclosed subject matter.

Referring now to FIGS. 7A and 7B, the pessary insertion apparatus 600 is shown in two operational configurations. In FIG. 7A, the pessary-engaging structure 206 is positioned within the body 602 in a collapsed configuration, in which the arms are held inward. In FIG. 7B, the body 602 has been translated proximally relative to the support member 604, exposing the pessary-engaging structure 206 through the slits 704 of the cap 702 and allowing the structure to move toward an expanded configuration. The arms may expand due to restoring force in the folded pessary device, resilience of the living hinges 310, or a combination thereof.

Referring now to FIGS. 8A-8C, interaction between the pessary-engaging structure 206 and a folded pessary device 802 is shown. In FIG. 8A, the folded pessary device 802 is engaged with the pessary-engaging structure 206 while the structure is in the collapsed configuration within the body 602. In some embodiments, where the pessary device includes a bulge 804, the bulge is positioned between curved portions of the first arm of the pessary-engaging structure 206.

In FIGS. 8B and 8C, translation of the body 602 proximally exposes the pessary-engaging structure 206, allowing the arms to move outward toward the expanded configuration and permitting the pessary device 802 to transition toward its unfolded shape. Subsequent rotation of the pessary-engaging structure 206 orients the pessary device 802 for placement. In some embodiments, the structure 206 can additionally tilt out of plane (e.g., about 10°-30°) to facilitate release of the pessary device within the vaginal fornix.

Figure 9A:
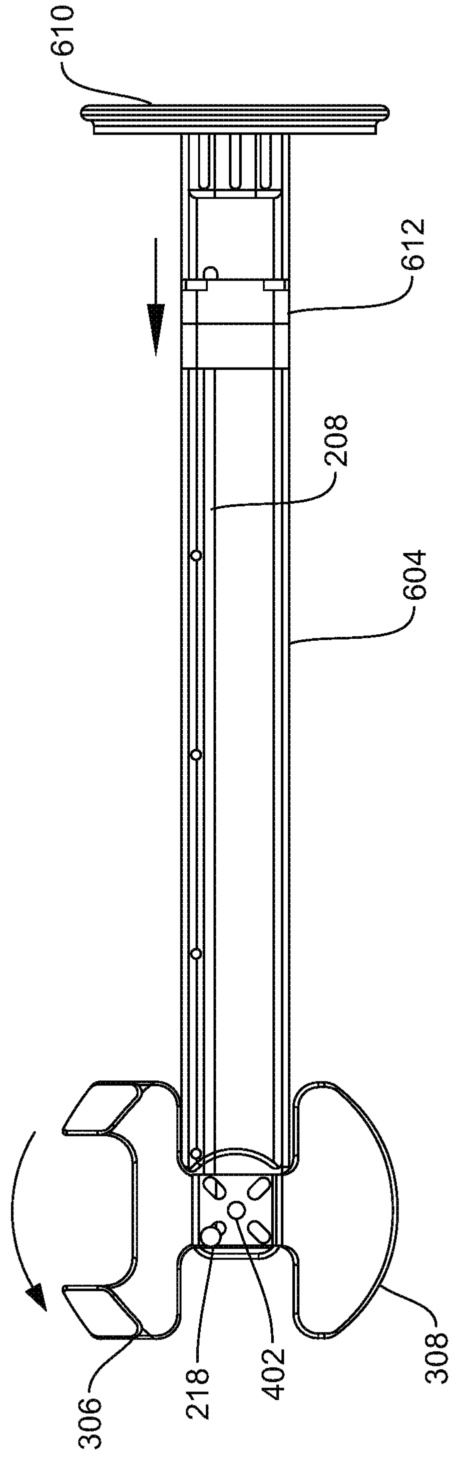
FIGS. 9A-9B depict top views illustrating a sequence of rotation of the pessary-engaging structure and associated actuation components of the pessary insertion apparatus in response to actuation, in accordance with the disclosed subject matter. For clarity, the body of the apparatus is omitted in these views.
Figure 9B:
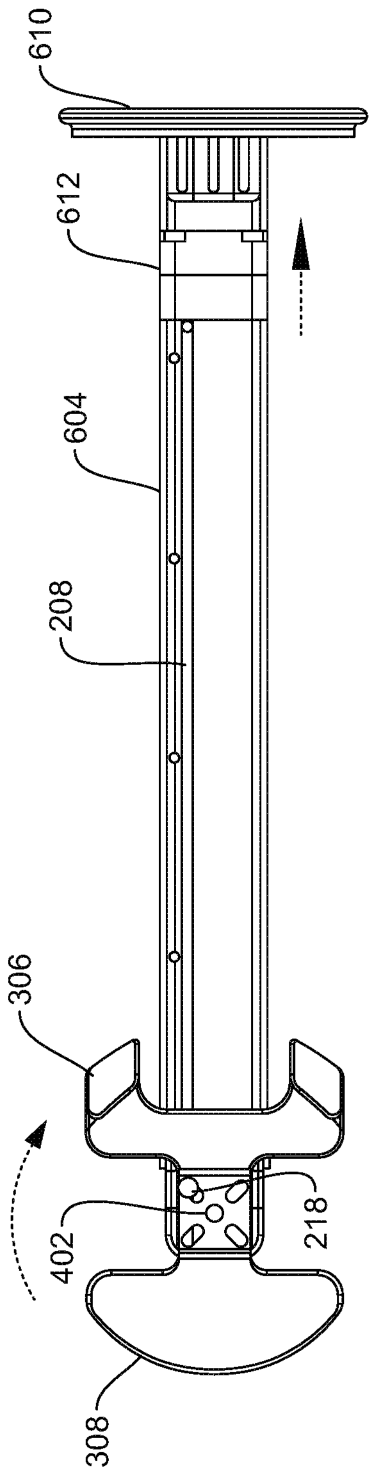

Referring now to FIGS. 9A and 9B, rotation of the pessary-engaging structure 206 relative to the support member 604 is shown with the body omitted for clarity. The middle member 312 is secured to the support member 604 via a pivot feature 402 that allows controlled rotation while preventing axial separation. The second rod end 218 engages the middle member 312 at an offset position, such that translation of the rod 208 applies a rotational moment. FIG. 9A illustrates a first angular orientation, and FIG. 9B illustrates a second angular orientation suitable for positioning and releasing the pessary device. In some embodiments, the rotational range is about 450 to 120°, such as about 90°, and can be performed clockwise or counter-clockwise.

Method of Loading and Operating the Pessary Insertion Apparatus

Figure 10:
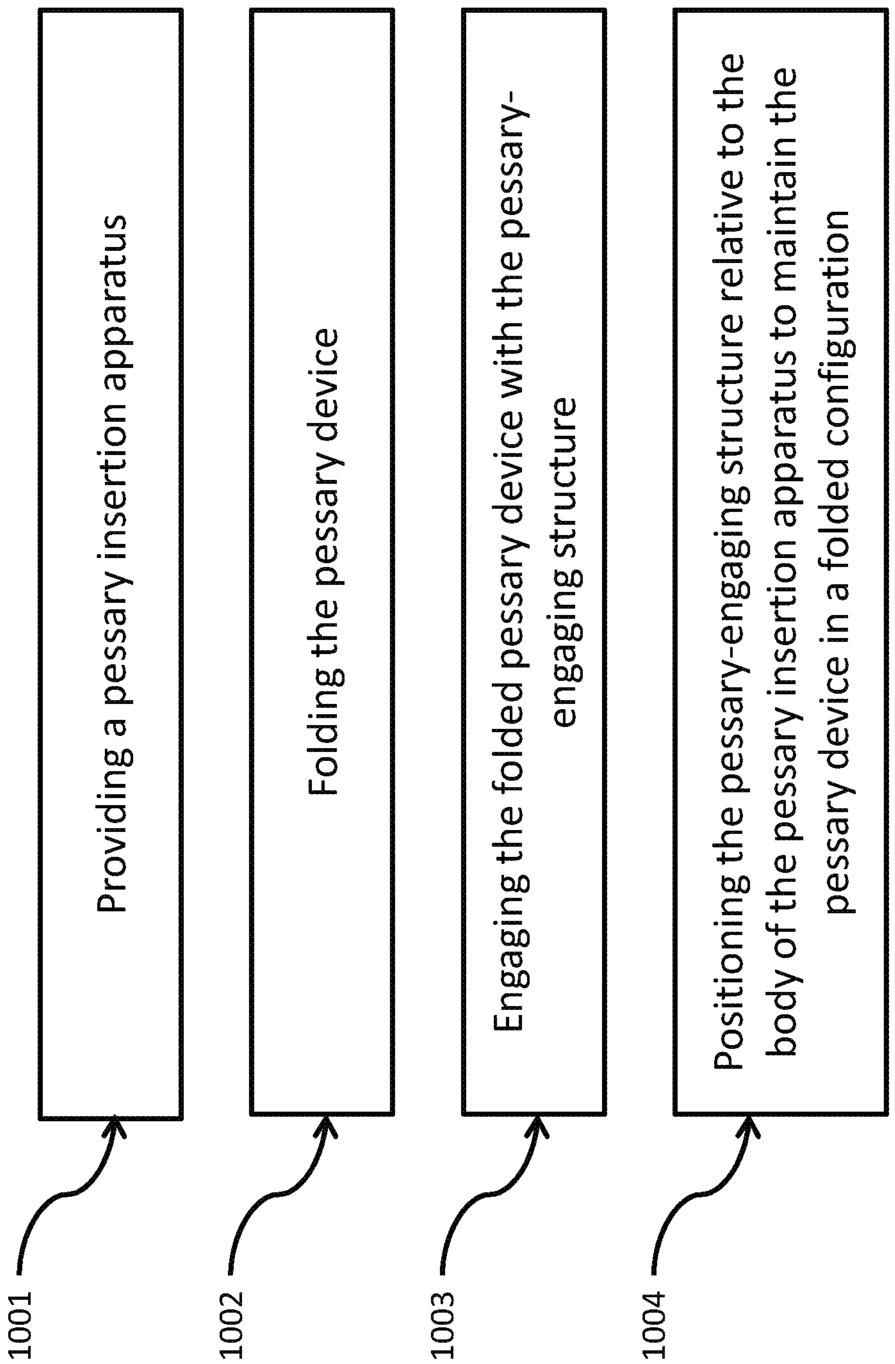
FIG. 10 is a flowchart of a method of installing a pessary device on a pessary insertion apparatus, in accordance with the disclosed subject matter.

Referring now to FIG. 10, a method of loading the pessary device onto a pessary insertion apparatus is provided. Unless otherwise specified, the steps described herein are not limited to any particular order and may occur in sequential or overlapping fashion. A step 1001, a pessary insertion apparatus (e.g., pessary insertion apparatus 200, 600) may be provided. At step 1002, the pessary device is folded, for example by manually bending opposing portions of the outer ring toward one another to form a U-shaped or crescent-shaped profile. Folding can be performed manually or by pressing the pessary device directly into the arms of the pessary-engaging structure such that the arms guide the deformation. In other embodiments, not shown, the pessary device may be loaded in the insertion apparatus prior to folding. In these embodiments, the pessary device may be folded after it contacts the pessary-engaging structure. In some embodiments, the pessary device is folded and/or rotated upon sliding the pessary device toward the proximal end, in one case placing or drawing the pessary into the body. In these embodiments, folding and/or rotating may be a consequence of movement of the engagement structures alone and/or user manipulation. In some embodiments, the pessary device is a ring pessary. In some embodiments, the pessary device is a ring with bulge pessary.

At step 1003, the folded pessary device can then be engaged with the pessary-engaging structure. Engagement can include positioning at least a portion of the outer ring within a receiving region defined by one or more curved portions of a first arm of the structure and positioning an opposite portion of the device against a planar surface of a second arm of the structure. In this state, the pessary device may partially relax from the initial manually folded configuration.

At step 1004, the pessary engaging structure can be positioned relative to the body of the pessary insertion apparatus to maintain the pessary device in a folded configuration. The user can hold the pessary-engaging structure (with pessary device) in its collapsed configuration while positioning the structure relative to the body of the apparatus. The user can translate the body of the apparatus relative to the support member (e.g., support member 204, 604) to draw the pessary-engaging structure into the interior of the body (e.g., body 202, 602). The translation direction depends on the loading orientation.

In some embodiments, the geometry of the body of the insertion apparatus can induce folding of the pessary device when the pessary-engaging structure is drawn into the body of the apparatus—or, depending upon the method of loading the apparatus within the body, when the pessary engaging structure is inserted into the body, as may be the case with the embodiment shown in FIGS. 6-8C. For example, a tapered, flared, or contoured internal surface of the body of the apparatus can progressively compress the pessary device into its folded configuration, thereby folding the pessary device without requiring the user to maintain the pessary device in a folded configuration.

In some embodiments, during engagement of the pessary device with the pessary-engaging structure, the pessary-engaging structure can be located between the first (proximal) end of the body and the handle (e.g., handle 210, 610). In such embodiments, positioning the structure includes translating the support member relative to the body of the apparatus such that the pessary-engaging structure moves towards the second (distal) end of the body. In other embodiments, during engagement, the pessary-engaging structure can be located beyond the second end of the body. In such embodiments, positioning the structure includes translating the support member relative to the body such that the pessary-engaging structure moves towards the first (proximal) end of the body. In either loading orientation, the body can be moved relative to the support member so as to enclose the pessary-engaging structure within the body, thereby maintaining the pessary-device in a folded configuration during handling and insertion of the apparatus into the vaginal canal. In the loaded configuration, the pessary-engaging structure and pessary device are positioned between the first and second end of the body after positioning.

The loaded pessary insertion apparatus can then be inserted into the vaginal canal with the second (distal) end of the body oriented toward the vaginal fornix. Insertion can continue until a tactile increase in resistance is perceived. With the second end of the body proximate the desired location, the pessary device can be deployed. Deployment can include translating the body toward the handle of the apparatus to expose the pessary-engaging structure, followed by rotation of the pessary-engaging structure (via actuator activation) to orient the pessary device for release. Upon exposure, the restoring force of the folded pessary device (and/or the restoring force of the pessary-engaging structure) can urge the arms of the structure toward an expanded configuration, enabling the pessary device to return towards its unfolded configuration and seat near the vaginal fornix. The pessary insertion apparatus can be withdrawn by pulling the body and/or the handle, leaving the pessary device in position.

Materials and Manufacturing

The disclosed pessary insertion apparatus can be manufactured of various materials by various methods. Materials selected for each of the components of the pessary insertion apparatus can be chosen to provide appropriate rigidity, flexibility, user comfort, and biocompatibility for insertion into the vagina. In many embodiments the materials of the apparatus include polymers, plastics, metals, alloys, ceramics, or combinations thereof. In many embodiments the apparatus is manufactured by 3D printing, injection molding, machining, milling, or combinations thereof.

The body can be formed from one or more materials (e.g., a combination thereof), including but not limited to a thermoplastic polymer such as polypropylene, polyethylene, polycarbonate, nylon, or blends or copolymers thereof. In some embodiments, the body is overmolded. The support member can be formed from one or more materials (e.g., a combination thereof), including but not limited to stainless steel, titanium, aluminum, or a polymer-coated metal. The pessary-engaging structure can be formed from one or more materials (e.g., a combination thereof), including but not limited to silicone, thermoplastic elastomers, thermoplastic polyurethane, latex-free elastomers, or medical-grade rubber.

The disclosure provides improved techniques for pessary insertion and deployment that may address various aspects of the deployment process. The methods described herein may involve folding a pessary device and engaging the folded device with a specialized insertion apparatus. The insertion apparatus may maintain the pessary device in a folded configuration during insertion, which may facilitate easier passage through the vaginal canal and positioning at or near the fornix.

Figure 11:
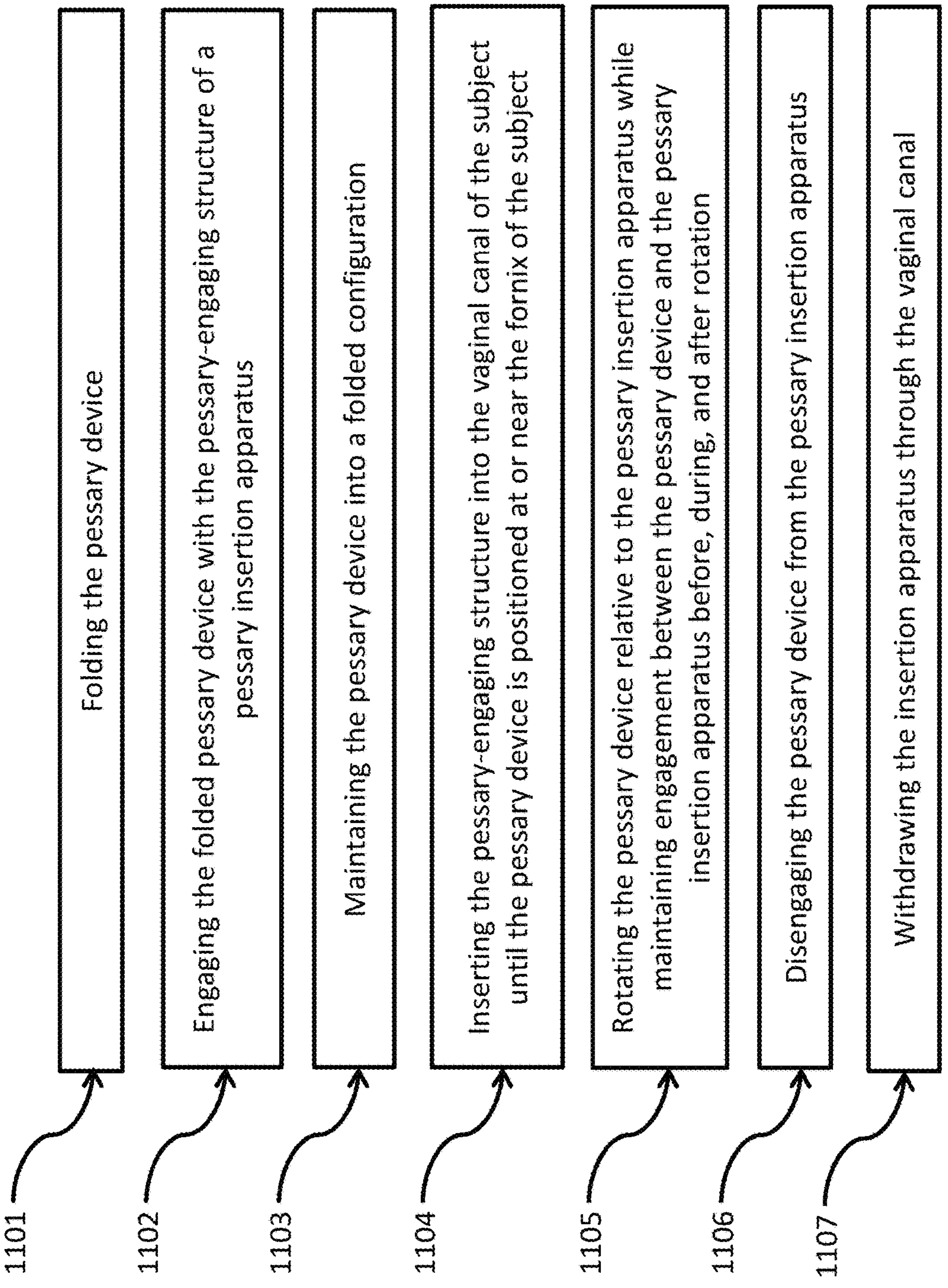
FIG. 11 is a flowchart of a method of deploying a pessary device from a pessary insertion apparatus, in accordance with the disclosed subject matter

Referring now to FIG. 11, a method of deploying a pessary device within a vaginal canal of a subject is provided. Unless otherwise specified, the steps described herein are not limited to any particular order and may occur in sequential or overlapping fashion. At step 1101, a pessary device can be folded. At step 1102, the folded pessary device can be engaged with the pessary-engaging structure of a pessary insertion apparatus. At step 1103, the pessary device can be maintained in a folded configuration. At step 1104, the pessary-engaging structure can be inserted into the vaginal canal of the subject until the pessary device is positioned at or near the fornix of the subject. At step 1105, the pessary device can be rotated relative to the pessary insertion apparatus while maintaining engagement between the pessary device and the pessary insertion apparatus before, during, and after rotation. At step 1106, the pessary device can be disengaged from the pessary insertion apparatus. At step 1107, the pessary insertion apparatus can be withdrawn through the vaginal canal.

The disclosed insertion methods may include rotating the pessary device relative to the insertion apparatus while maintaining engagement between the components. Following appropriate positioning, the pessary device may be disengaged from the insertion apparatus, and the insertion apparatus may be withdrawn from the vaginal canal.

The method of deploying a pessary device within a vaginal canal may begin with folding the pessary device to reduce the profile and facilitate insertion. The folding process may involve compressing or bending the pessary device into a more compact configuration that allows for easier passage through the vaginal canal while minimizing patient discomfort.

Following the folding step, the folded pessary device may be engaged with a pessary-engaging structure of a pessary insertion apparatus. The pessary-engaging structure may be configured to securely hold the pessary device while maintaining the folded configuration throughout the insertion process. The engagement between the pessary device and the pessary-engaging structure may provide stable retention that prevents premature deployment or displacement during insertion.

The pessary insertion apparatus may maintain the pessary device in the folded configuration during the insertion procedure. This maintenance of the folded state may allow for controlled deployment and may prevent the pessary device from expanding or unfolding prematurely within the vaginal canal. The insertion process may involve advancing the pessary-engaging structure into the vaginal canal of the subject until the pessary device reaches the desired location.

The insertion may continue until the pessary device is positioned at or near the fornix of the subject. The fornix represents the deepest portion of the vaginal canal, and positioning at or near this anatomical landmark may provide appropriate placement for various therapeutic applications. The depth of insertion may be determined based on anatomical considerations and the specific clinical requirements for the pessary device placement.

During the deployment process, the method may include rotating the pessary device relative to the pessary insertion apparatus while maintaining engagement between the pessary device and the pessary insertion apparatus. This rotation may occur before, during, and after the rotational movement, allowing for precise orientation of the pessary device within the vaginal canal. The maintained engagement during rotation may provide controlled manipulation of the pessary device position without losing contact between the components.

The rotation step may facilitate proper alignment of the pessary device within the vaginal canal, and at or near the fornix, and may allow for optimal positioning relative to the pelvic organs. The ability to rotate while maintaining engagement may provide the user/practitioner with enhanced control over the final placement and orientation of the pessary device.

Following appropriate positioning and any necessary rotational adjustments, the pessary device may be disengaged from the pessary insertion apparatus. The disengagement process may involve releasing the connection between the pessary-engaging structure and the pessary device, allowing the pessary device to assume its deployed configuration within the vaginal canal. The disengagement may be accomplished through various mechanisms that allow for controlled release of the pessary device, for example compression of the walls of the vaginal canal around and about the pessary device.

After disengagement of the pessary device, the insertion apparatus may be withdrawn through the vaginal canal. The withdrawal process may involve carefully removing the pessary insertion apparatus while leaving the pessary device in the desired position within the vaginal canal. The withdrawal may be performed in a manner that minimizes disturbance to the positioned pessary device and maintains patient comfort during the removal of the insertion apparatus.

In addition to the deployment methods, the disclosure encompasses pessary insertion kits that may include various components to facilitate the insertion process. Such kits may comprise a pessary insertion apparatus along with instructions for use. The kits may further include one or more pessary devices, and in some cases, multiple pessary devices of varying configurations may be provided to accommodate different patient needs or clinical situations.

The kits may also include multiple pessary engaging structures or pessary engaging structure arms of differing sizes, which may allow for compatibility with various pessary device configurations. Some implementations of the kits may include a body for housing the pessary insertion apparatus (as described above) and related components, which may facilitate storage, organization, and/or use of the kit contents and components.

The described pessary insertion kit may comprise a pessary insertion apparatus and instructions for use. The instructions for use may provide guidance for clinicians regarding proper deployment techniques, safety considerations, and procedural steps for pessary insertion. The instructions may include detailed procedural information, anatomical considerations, and guidelines for patient preparation and post-insertion care, such as those described above.

The pessary insertion kit may further comprise a pessary device configured for deployment using the pessary insertion apparatus. The pessary device may be selected based on patient-specific requirements and/or clinical indications. In some cases, the kit may include multiple pessary devices to provide options for different clinical situations or patient anatomical variations.

Some implementations of the pessary insertion kit may comprise two or more pessary devices. The multiple pessary devices may include different sizes, configurations, or therapeutic designs to accommodate varying patient needs. The inclusion of multiple pessary devices may allow clinicians to select the most appropriate device based on individual patient anatomy, clinical condition, or treatment objectives. The multiple devices may provide backup options in case of procedural complications or may offer different therapeutic approaches for various clinical scenarios.

The pessary insertion kit may comprise a plurality of pessary engaging structures or pessary engaging structure arms of differing sizes. The different sizes of pessary engaging structures may accommodate various pessary device dimensions and configurations. The plurality of engaging structures may allow for compatibility with different pessary types, sizes, or designs that may be encountered in clinical practice. The varying sizes of pessary engaging structure arms may provide flexibility in engaging different pessary devices and may allow for secure retention of devices with different dimensional characteristics.

In some cases, the pessary insertion kit may comprise a body for containing the pessary insertion apparatus, as described above. The body may provide organized storage for the insertion apparatus and related components. The body may facilitate insertion by providing an anatomically appropriate shell for the apparatus components.

The body may be configured to accommodate the pessary insertion apparatus along with any additional kit components such as variously sized pessary devices. The design of the body may allow for efficient insertion while maintaining the pessary device's engagement by the insertion apparatus. The design of the body may also allow for maintaining the pessary device in the folded state.

The operation of the pessary insertion system may involve coordinated interaction between the practitioner/user, the insertion apparatus, and the pessary device to achieve successful deployment. The user or practitioner may initiate the procedure by preparing the pessary device through folding to achieve a reduced profile configuration. This preparation step may allow the user or practitioner to manipulate the pessary device into a form that facilitates engagement with the insertion apparatus and minimizes discomfort during insertion into the vaginal canal.

The engagement process may involve the user or practitioner positioning the folded pessary device in contact with the pessary-engaging structure of the insertion apparatus. The practitioner may apply appropriate pressure or manipulation to secure the connection between the pessary device and the engaging structure. The insertion apparatus may respond to this engagement by maintaining the folded configuration of the pessary device through mechanical retention or constraint mechanisms, for example positioning within the body.

During the insertion phase, the user or practitioner may guide the insertion apparatus into the vaginal canal while the apparatus and/or the body maintains the pessary device's position and folded state.

1. A pessary insertion apparatus comprising: a support member having a first end and a second end; a handle coupled to the first end of the support member; a pessary-engaging structure disposed at the second end of the support member; and an actuator operatively coupled to the pessary-engaging structure and configured to translate a force applied to the actuator into rotation of the pessary-engaging structure.
2. The pessary insertion apparatus of embodiment 1, further comprising a body having a first end and a second end, wherein the pessary-engaging structure comprises a plurality of arms and a middle member, each one of the plurality of arms coupled to the middle member.
3. The pessary insertion apparatus of embodiment 1 or embodiment 2, wherein at least one of the plurality of arms is joined to the middle member by a living hinge.
4. The pessary insertion apparatus of any one of the previously recited apparatus embodiments, wherein the plurality of arms comprises a first arm and a second arm, each extending from the middle member.
5. The pessary insertion apparatus of any one of the previously recited apparatus embodiments, wherein the first arm comprises a first and a second curved portion arranged to define a receiving region for retaining a pessary device.
6. The pessary insertion apparatus of any one of the previously recited apparatus embodiments, wherein the second arm comprises a planar surface.
7. The pessary insertion apparatus of any one of the previously recited apparatus embodiments, wherein the body comprises an opening at the first end of the body and a cap at the second end of the body, the cap having a plurality of compliant flaps configured to flex to allow passage of the pessary-engaging structure.
8. The pessary insertion apparatus of any one of the previously recited apparatus embodiments, wherein the body defines a first opening at the first end of the body and a second opening at the second end of the body.
9. The pessary insertion apparatus of any one of the previously recited apparatus embodiments, wherein the longitudinal axis of the support member extends longitudinally within the body.
10. The pessary insertion apparatus of any one of the previously recited apparatus embodiments, wherein the support member is configured to translate relative to the body.
11. The pessary insertion apparatus of any one of the previously recited apparatus embodiments, wherein the body comprises a guide channel configured to guide translation of the body.
12. The pessary insertion apparatus of any one of the previously recited apparatus embodiments, wherein the actuator is disposed on the support member between the pessary-engaging structure and the handle.
13. The pessary insertion apparatus of any one of the previously recited apparatus embodiments, wherein the handle is disposed between the pessary-engaging structure and the actuator and the rod extends through the handle.
14. The pessary insertion apparatus of any one of the previously recited apparatus embodiments, further comprising a rod having a first end and a second end, the first end operatively coupled to the actuator and the second end operatively coupled to the pessary-engaging structure.
15. A method of installing a pessary device on a pessary insertion apparatus, comprising: providing a pessary insertion apparatus, the pessary insertion apparatus comprising: a body having a first end and a second end, a support member disposed at least partially within the body and configured to translate relative to the body, a handle coupled to the first end of the support member, a pessary-engaging structure disposed at the second end of the support member, wherein the first end of the body is positioned toward the handle and the second end is positioned away from the handle; folding the pessary device; engaging the folded pessary device with the pessary-engaging structure; and positioning the pessary-engaging structure relative to the body of the pessary insertion apparatus to maintain the pessary device in a folded configuration.
16. The method of embodiment 15, wherein engaging the folded pessary device with the pessary-engaging structure occurs when the pessary-engaging structure is positioned between the first end of the body and the handle.

17. The method of embodiment 15 or embodiment 16, wherein positioning the pessary-engaging structure relative to the body comprises translating the support member relative to the body such that the pessary-engaging structure moves towards the second end of the body.
18. The method of any one of the previously recited method embodiments, wherein engaging the folded pessary device with the pessary-engaging structure occurs when the pessary-engaging structure is positioned beyond the second end of the body.
19. The method of any one of the previously recited method embodiments, wherein positioning the pessary-engaging structure relative to the body comprises translating the support member relative to the body such that the pessary-engaging structure moves towards the first end of the body.
20. The method of any one of the previously recited method embodiments, wherein the pessary-engaging structure is positioned between the first end and second end of the body after positioning.
21. The method of any one of the previously recited method embodiments, further comprising deploying the pessary device by translating the support member relative to the body such that the pessary-engaging structure becomes exposed through the second end of the body and the pessary device transitions from the folded configuration toward an unfolded configuration.
22. A method of deploying a pessary device within a vaginal canal of a subject, comprising: folding the pessary device; engaging the folded pessary device with a pessary-engaging structure of a pessary insertion apparatus; maintaining the pessary device in a folded configuration; inserting the pessary-engaging structure into the vaginal canal of the subject until the pessary device is positioned at or near the fornix of the subject; rotating the pessary device relative the pessary insertion apparatus while maintaining engagement between the pessary device and the pessary insertion apparatus before during and after rotation; disengaging the pessary device from the pessary insertion apparatus; and withdrawing the insertion apparatus through the vaginal canal.
23. The method of embodiment 22, wherein the pessary insertion apparatus is as described in any of the previously recited apparatus embodiments or the specification.
24. A pessary insertion kit comprising: a pessary insertion apparatus, and instructions for use.
25. The pessary insertion kit, further comprising a pessary device.
26. The pessary insertion kit of any one of the previously recited kit embodiments, comprising two or more pessary devices.
27. The pessary insertion kit of any one of the previously recited kit embodiments, comprising a plurality of pessary engaging structures or pessary engaging structure arms of differing sizes.
28. The pessary insertion kit of any one of the previously recited kit embodiments, comprising a body for containing the pessary insertion apparatus.

While the disclosed subject matter is described herein in terms of certain preferred embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A pessary insertion apparatus comprising:

a support member having a first end and a second end;

a handle coupled to the first end of the support member;

a pessary-engaging structure disposed at the second end of the support member, wherein the pessary-engaging structure comprises a plurality of arms and a middle member, each one of the plurality of arms coupled to the middle member;

an actuator operatively coupled to the pessary-engaging structure and configured to translate a force applied to the actuator into rotation of the pessary-engaging structure; and a body having a first end and a second end, wherein the body comprises an opening at the first end of the body and a cap at the second end of the body, the cap having a plurality of compliant flaps configured to flex to allow passage of the pessary-engaging structure.

2. The pessary insertion apparatus of claim 1, wherein at least one of the plurality of arms is joined to the middle member by a living hinge.

3. The pessary insertion apparatus of claim 1, wherein the plurality of arms comprises a first arm and a second arm, each extending from the middle member.

4. The pessary insertion apparatus of claim 3, wherein the first arm comprises a first curved portion and a second curved portion arranged to define a receiving region for retaining a pessary device.

5. The pessary insertion apparatus of claim 3, wherein the second arm comprises a planar surface.

6. The pessary insertion apparatus of claim 1, wherein the body defines a first opening at the first end of the body and a second opening at the second end of the body.

7. The pessary insertion apparatus of claim 1, wherein a longitudinal axis of the support member extends longitudinally within the body.

8. The pessary insertion apparatus of claim 1, wherein the support member is configured to translate relative to the body.

9. The pessary insertion apparatus of claim 1, wherein the body comprises a guide channel configured to guide translation of the body relative to the support member.

10. The pessary insertion apparatus of claim 1, wherein the actuator is disposed on the support member between the pessary-engaging structure and the handle.

11. The pessary insertion apparatus of claim 1, wherein the handle is disposed between the pessary-engaging structure and the actuator and a rod extends through the handle.

12. The pessary insertion apparatus of claim 1, further comprising a rod having a first end and a second end, the first end operatively coupled to the actuator and the second end operatively coupled to the pessary-engaging structure.

13. A method of installing a pessary device on a pessary insertion apparatus, comprising:

providing a pessary insertion apparatus, the pessary insertion apparatus comprising:

a body having a first end and a second end, wherein the body comprises an opening at the first end of the body and a cap at the second end of the body, a support member disposed at least partially within the body and configured to translate relative to the body, a handle coupled to the first end of the support member, a pessary-engaging structure disposed at the second end of the support member, wherein the pessary-engaging structure comprises a plurality of arms and a middle member, each one of the plurality of arms coupled to the middle member, and an actuator operatively coupled to the pessary-engaging structure and configured to translate a force applied to the actuator into rotation of the pessary-engaging structure, wherein the first end of the body is positioned toward the handle and the second end of the body is positioned away from the handle, and wherein the cap has a plurality of compliant flaps configured to flex to allow passage of the pessary-engaging structure;

folding the pessary device;

engaging the folded pessary device with the pessary-engaging structure; and positioning the pessary-engaging structure relative to the body of the pessary insertion apparatus to maintain the pessary device in a folded configuration.

14. The method of claim 13, wherein engaging the folded pessary device with the pessary-engaging structure occurs when the pessary-engaging structure is positioned between the first end of the body and the handle.

15. The method of claim 14, wherein positioning the pessary-engaging structure relative to the body comprises translating the support member relative to the body such that the pessary-engaging structure moves towards the second end of the body.

16. The method of claim 13, wherein engaging the folded pessary device with the pessary-engaging structure occurs when the pessary-engaging structure is positioned beyond the second end of the body, and wherein the method further comprises:

deploying the pessary device by translating the support member relative to the body such that the pessary-engaging structure becomes exposed through the second end of the body and the pessary device transitions from the folded configuration toward an unfolded configuration.

17. The method of claim 16, wherein positioning the pessary-engaging structure relative to the body comprises translating the support member relative to the body such that the pessary-engaging structure moves towards the first end of the body.

18. A method of deploying a pessary device within a vaginal canal of a subject, comprising:

folding the pessary device;

engaging the folded pessary device with a pessary-engaging structure of a pessary insertion apparatus, the pessary insertion apparatus comprising:

a support member having a first end and a second end, a handle coupled to the first end of the support member, a pessary-engaging structure disposed at the second end of the support member, wherein the pessary-engaging structure comprises a plurality of arms and a middle member, each one of the plurality of arms coupled to the middle member, an actuator operatively coupled to the pessary-engaging structure and configured to translate a force applied to the actuator into rotation of the pessary-engaging structure, and a body having a first end and a second end, wherein the body comprises an opening at the first end of the body and a cap at the second end of the body, the cap having a plurality of compliant flaps configured to flex to allow passage of the pessary-engaging structure;

maintaining the pessary device in a folded configuration;

inserting the pessary-engaging structure into the vaginal canal of the subject until the pessary device is positioned at or near a vaginal fornix of the subject;

rotating the pessary device relative to the pessary insertion apparatus while maintaining engagement between the pessary device and the pessary insertion apparatus before, during, and after rotation;

disengaging the pessary device from the pessary insertion apparatus; and withdrawing the pessary insertion apparatus through the vaginal canal.

* * * * *